US012093023B2

(12) United States Patent
Akella

(10) Patent No.: US 12,093,023 B2
(45) Date of Patent: Sep. 17, 2024

(54) WORKSPACE ACTOR COORDINATION SYSTEMS AND METHODS

(71) Applicant: R4N63R Capital LLC, Wilmington, DE (US)

(72) Inventor: Prasad Narasimha Akella, Palo Alto, CA (US)

(73) Assignee: R4N63R CAPITAL LLC, Wilmington, DE (US)

( * ) Notice: Subject to any disclaimer, the term of this patent is extended or adjusted under 35 U.S.C. 154(b) by 718 days.

(21) Appl. No.: 16/181,253

(22) Filed: Nov. 5, 2018

(65) Prior Publication Data

US 2019/0138967 A1 May 9, 2019

Related U.S. Application Data

(60) Provisional application No. 62/581,541, filed on Nov. 3, 2017.

(51) Int. Cl.
*G06Q 10/06* (2023.01)
*G05B 19/418* (2006.01)
(Continued)

(52) U.S. Cl.
CPC ... *G05B 19/4183* (2013.01); *G05B 19/41835* (2013.01); *G06F 9/4498* (2018.02);
(Continued)

(58) Field of Classification Search
None
See application file for complete search history.

(56) References Cited

U.S. PATENT DOCUMENTS 6,963,827 B1 11/2005 Elyea et al.
7,401,728 B2 * 7/2008 Markham ............. G06Q 10/00
235/375
(Continued)

FOREIGN PATENT DOCUMENTS

CN 106094707 A * 11/2016
CN 107066979 A * 8/2017 ......... G06K 9/00335
(Continued)

OTHER PUBLICATIONS

T. Ko, "A survey on behavior analysis in video surveillance for homeland security applications," 2008 37th IEEE Applied Imagery Pattern Recognition Workshop, Washington, DC, USA, 2008, pp. 1-8, doi: 10.1109/AIPR.2008.4906450 (Year: 2008).*

(Continued)

*Primary Examiner* — Mehmet Yesildag
(74) *Attorney, Agent, or Firm* — Dorsey & Whitney LLP

(57) ABSTRACT

Workspace coordination systems and methods are presented. A method can comprise: accessing in real time respective information associated with a first actor and a second actor, including sensed activity information; analyzing the information, including analyzing activity of the first actor with respect to a second actor; and forwarding respective feedback based on the results of the analysis. The feedback can includes an individual objective specific to one of either the first actor or the second actor. The feedback includes collective objective with respect to the first actor or the second actor. The analyzing can include automated artificial intelligence analysis. Sensed activity information can be associated with a grid within the activity space. It is appreciated there can be various combinations of actors (e.g., human and device, device and device, human and human, etc.). The feedback can be a configuration layout suggestion. The (Continued)

feedback can be a suggested assignment of a type of actor to an activity.

29 Claims, 23 Drawing Sheets

(51) Int. Cl.

| | | |
|---|---|---|
| G06F 9/448 | (2018.01) | |
| G06F 9/48 | (2006.01) | |
| G06F 11/07 | (2006.01) | |
| G06F 11/34 | (2006.01) | |
| G06F 16/22 | (2019.01) | |
| G06F 16/23 | (2019.01) | |
| G06F 16/2455 | (2019.01) | |
| G06F 16/901 | (2019.01) | |
| G06F 16/9035 | (2019.01) | |
| G06F 16/904 | (2019.01) | |
| G06F 30/20 | (2020.01) | |
| G06F 30/23 | (2020.01) | |
| G06F 30/27 | (2020.01) | |
| G06N 3/008 | (2023.01) | |
| G06N 3/04 | (2023.01) | |
| G06N 3/044 | (2023.01) | |
| G06N 3/045 | (2023.01) | |
| G06N 3/08 | (2023.01) | |
| G06N 3/084 | (2023.01) | |
| G06N 7/01 | (2023.01) | |
| G06N 20/00 | (2019.01) | |
| G06Q 10/0631 | (2023.01) | |
| G06Q 10/0639 | (2023.01) | |
| G06T 19/00 | (2011.01) | |
| G06V 10/25 | (2022.01) | |
| G06V 10/44 | (2022.01) | |
| G06V 10/82 | (2022.01) | |
| G06V 20/52 | (2022.01) | |
| G06V 40/20 | (2022.01) | |
| G09B 19/00 | (2006.01) | |
| B25J 9/16 | (2006.01) | |
| G01M 99/00 | (2011.01) | |
| G05B 19/423 | (2006.01) | |
| G05B 23/02 | (2006.01) | |
| G06F 18/21 | (2023.01) | |
| G06F 111/10 | (2020.01) | |
| G06F 111/20 | (2020.01) | |
| G06N 3/006 | (2023.01) | |
| G06Q 10/083 | (2023.01) | |
| G06Q 50/26 | (2012.01) | |
| G16H 10/60 | (2018.01) | |

(52) U.S. Cl.
CPC ........ *G06F 9/4881* (2013.01); *G06F 11/0721* (2013.01); *G06F 11/079* (2013.01); *G06F 11/3452* (2013.01); *G06F 16/2228* (2019.01); *G06F 16/2365* (2019.01); *G06F 16/24568* (2019.01); *G06F 16/9024* (2019.01); *G06F 16/9035* (2019.01); *G06F 16/904* (2019.01); *G06F 30/20* (2020.01); *G06F 30/23* (2020.01); *G06F 30/27* (2020.01); *G06N 3/008* (2013.01); *G06N 3/04* (2013.01); *G06N 3/044* (2023.01); *G06N 3/045* (2023.01); *G06N 3/08* (2013.01); *G06N 3/084* (2013.01); *G06N 7/01* (2023.01); *G06N 20/00* (2019.01); *G06Q 10/06* (2013.01); *G06Q 10/063112* (2013.01); *G06Q 10/06316* (2013.01); *G06Q 10/06393* (2013.01); *G06Q 10/06395* (2013.01); *G06Q 10/06398* (2013.01); *G06T 19/006* (2013.01); *G06V 10/25* (2022.01); *G06V 10/454* (2022.01); *G06V 10/82* (2022.01); *G06V 20/52* (2022.01); *G06V 40/20* (2022.01); *G09B 19/00* (2013.01); *B25J 9/1664* (2013.01); *B25J 9/1697* (2013.01); *G01M 99/005* (2013.01); *G05B 19/41865* (2013.01); *G05B 19/423* (2013.01); *G05B 23/0224* (2013.01); *G05B 2219/32056* (2013.01); *G05B 2219/36442* (2013.01); *G06F 18/217* (2023.01); *G06F 2111/10* (2020.01); *G06F 2111/20* (2020.01); *G06N 3/006* (2013.01); *G06Q 10/083* (2013.01); *G06Q 50/26* (2013.01); *G16H 10/60* (2018.01)

(56) References Cited

U.S. PATENT DOCUMENTS

| | | | |
|---|---|---|---|
| 8,260,783 | B2 | 9/2012 | Milam |
| 8,306,931 | B1 | 11/2012 | Bowman et al. |
| 9,305,216 | B1 | 4/2016 | Mishra |
| 9,471,610 | B1 | 10/2016 | Long et al. |
| 9,921,726 | B1 | 3/2018 | Sculley et al. |
| 10,445,702 | B1 | 10/2019 | Hunt |
| 10,713,794 | B1 | 7/2020 | He et al. |
| 10,852,712 | B2 | 12/2020 | Ben-Bassat et al. |
| 11,226,720 | B1* | 1/2022 | Vandivere ............ G06F 3/0482 |
| 2003/0229471 | A1 | 12/2003 | Guralnik et al. |
| 2005/0105765 | A1 | 5/2005 | Han et al. |
| 2006/0224254 | A1 | 10/2006 | Rumi et al. |
| 2006/0241792 | A1 | 10/2006 | Pretlove et al. |
| 2006/0271526 | A1 | 11/2006 | Charnock et al. |
| 2009/0016599 | A1 | 1/2009 | Eaton et al. |
| 2009/0016600 | A1 | 1/2009 | Eaton et al. |
| 2009/0089227 | A1 | 4/2009 | Sturrock et al. |
| 2010/0082512 | A1 | 4/2010 | Myerson et al. |
| 2011/0043626 | A1 | 2/2011 | Cobb et al. |
| 2012/0197898 | A1 | 8/2012 | Pandey et al. |
| 2012/0225413 | A1 | 9/2012 | Kotranza et al. |
| 2013/0234854 | A1 | 9/2013 | Mukherjee et al. |
| 2013/0307693 | A1 | 11/2013 | Stone et al. |
| 2013/0339923 | A1 | 12/2013 | Xu et al. |
| 2014/0003710 | A1 | 1/2014 | Seow et al. |
| 2014/0079297 | A1 | 3/2014 | Tadayon et al. |
| 2014/0172357 | A1 | 6/2014 | Heinonen |
| 2014/0222813 | A1 | 8/2014 | Yang et al. |
| 2014/0275888 | A1 | 9/2014 | Wegerich et al. |
| 2014/0277593 | A1 | 9/2014 | Nixon et al. |
| 2014/0279776 | A1 | 9/2014 | Brown et al. |
| 2014/0326084 | A1 | 11/2014 | Bhushan |
| 2014/0337000 | A1 | 11/2014 | Asenjo et al. |
| 2014/0379156 | A1 | 12/2014 | Kamel et al. |
| 2015/0110388 | A1 | 4/2015 | Eaton et al. |
| 2015/0363438 | A1 | 12/2015 | Botelho |
| 2015/0363741 | A1 | 12/2015 | Chandra et al. |
| 2015/0364158 | A1 | 12/2015 | Gupte et al. |
| 2016/0085607 | A1 | 3/2016 | Marr et al. |
| 2016/0322078 | A1 | 11/2016 | Bose et al. |
| 2016/0375524 | A1 | 12/2016 | Hsu |
| 2017/0098161 | A1* | 4/2017 | Ellenbogen .......... G06K 9/6273 |
| 2017/0232613 | A1 | 8/2017 | Ponulak et al. |
| 2017/0243154 | A1* | 8/2017 | Fletter ............ G06Q 10/063118 |
| 2017/0245806 | A1 | 8/2017 | Elhawary et al. |
| 2017/0262697 | A1 | 9/2017 | Kaps et al. |
| 2017/0308800 | A1 | 10/2017 | Cichon et al. |
| 2017/0320102 | A1* | 11/2017 | McVaugh ............... B07C 3/008 |
| 2018/0011973 | A1 | 1/2018 | Fish et al. |
| 2018/0039745 | A1 | 2/2018 | Chevalier et al. |
| 2018/0056520 | A1 | 3/2018 | Ozaki et al. |
| 2018/0059630 | A1 | 3/2018 | Yang et al. |
| 2018/0139309 | A1 | 5/2018 | Pasam et al. |
| 2018/0324199 | A1 | 11/2018 | Crotinger et al. |
| 2018/0330250 | A1 | 11/2018 | Nakayama et al. |
| 2018/0330287 | A1 | 11/2018 | Tripathi |
| 2019/0034734 | A1 | 1/2019 | Yen et al. |

(56) References Cited

U.S. PATENT DOCUMENTS

| | | | |
|---|---|---|---|
| 2019/0058719 | A1 | 2/2019 | Kar et al. |
| 2019/0138971 | A1 | 5/2019 | Uggirala et al. |
| 2019/0320898 | A1 | 10/2019 | Dirghangi et al. |
| 2020/0051203 | A1 | 2/2020 | Nurvitadhi et al. |
| 2020/0128307 | A1 | 4/2020 | Li |
| 2020/0293972 | A1 | 9/2020 | Arao et al. |

FOREIGN PATENT DOCUMENTS

| | | | |
|---|---|---|---|
| EP | 2626757 | | 8/2013 |
| EP | 2996006 | A1 | 3/2016 |
| WO | 2012-141601 | | 10/2012 |
| WO | WO2017040167 | | 3/2017 |
| WO | WO-2017091883 | A1 * | 6/2017 ......... G06F 17/2785 |
| WO | WO-2018009405 | A1 * | 1/2018 ........... G06K 9/3233 |

OTHER PUBLICATIONS

L. Chen, J. Hoey, C. D. Nugent, D. J. Cook and Z. Yu, "Sensor-Based Activity Recognition," in IEEE Transactions on Systems, Man, and Cybernetics, Part C (Applications and Reviews), vol. 42, No. 6, pp. 790-808, Nov. 2012, doi: 10.1109/TSMCC.2012.2198883 (Year: 2012).*

Sepp Hochreiter & Jurgen Schmidhuber, *Long Short-Term memory*, Neural Computation, vol. 9, Issue 8, p. 1735-1780, Nov. 15, 1997.

Matthew Zeiler & Rob Fergus, Visualizing and Understanding Convolution Networks, arXiv;1311.2901v3, Nov. 28, 2013, pp. 11.

Ross Girshick, *Fast R-CNN*, Proceedings of the 2015 IEEE International Conference on Computer Vision (ICCV), p. 1440-1448, Dec. 7-13, 2015.

Shaoqing Ren et al., *Faster R-CNN: Towards Real Time Object Detection with Region Proposal Networks*, Proceedings of the 28th International Conference on Neural Information Processing Systems, vol. 1. p. 91-99, Dec. 7-12, 2015.

Christian Szegedy et al., *Inception-v4, Inception-Resnet and the Impact of Residual Connections on Learning*, ICLR 2016 Workshop, Feb. 18, 2016.

Jonathan Huang et al., *Speed/Accuracy Trade-Offs for Modern Convolutional Object Detectors*, Proceedings of the 2017 IEEE Conference on Computer Vision and Pattern Recognition (CVPR), Nov. 9, 2017.

Grinciunaite, et al., "Human Pose Estimation in Space and Time Using 3d cnn", European Conference on Computer Vision. Cham: Springer International Publishing, 2016. (Year:2016).

Ji, et al., "3D Convolutional Neural Networks for Human Action Recognition", IEEE Transactions on Pattern Analysis and Machine Intelligence 35.1 (2012): 221-231. (Year: 2012).

Zhang, et al., "Probabilistic Graphlet Transfer for Photo Cropping", IEEE Transactions on Image Processing 22.2 (2012):802-815 (Year: 2012).

* cited by examiner 1100
1110
Accessing associated with a first actor and a second actor, including sensed activity information.
1120
Analyzing the information, including analyzing activity of the first actor with respect to a second actor.
1130
Forwarding respective feedback based on the results of the analysis.
FIG. 11

1200

1210
Accessing information associated with a first actor and second actor, including sensed activity information within an activity space with respect to performing an activity.

1220
Analyzing the activity information, including analyzing activity of the first actor and analyzing activity of the second actor.

1230
Forwarding respective feedback in real time based on the results of the analysis to the first actor and the second actor, wherein the feedback includes a direction/command to change activity of the first actor or second actor and is based on the prediction.

FIG. 12

| DATE & TIME | ACTION IDENTIFIED | STARTING COORDINATES | | | ENDING COORDINATES | | | WEIGHT | MOVEMENT DISTANCE (cm) |
|---|---|---|---|---|---|---|---|---|---|
| | | x | y | z | x1 | y1 | z1 | | P(x, y, z) - P(x1, y1, z1) |
| 23 Oct 17 | | | | | | | | | |
| 7:03:03 AM | Grab screwdriver | 32 | -2 | 12 | 22 | 21 | 21 | 2 lbs | 26.65 |
| 7:03:06 AM | Grab screws | -22 | -21 | 21 | -12 | -55 | 12 | | 43.12 |
| 7:03:08 AM | Unknown | 12 | 4 | 2 | 12 | 4 | 2 | | 38.95 |
| 7:03:12 AM | Affix 4 screws | 35 | -2 | 12 | 22 | 21 | 21 | 2 lbs | 5.44 |
| 7:03:16 AM | Grab chassis | -12 | -21 | 21 | -12 | -55 | 12 | 3 lbs | 34.23 |
| 7:03:22 AM | Unknown | 22 | 4 | 2 | 12 | 4 | 2 | | 26.65 |
| 7:03:28 AM | Position fans | 32 | -2 | 12 | 22 | 21 | 21 | | 2.12 |
| 7:03:36 AM | Screw fan 1 | -2 | -21 | 21 | -12 | -55 | 12 | 2 lbs | 5.21 |
| 7:03:46 AM | Screw fan 2 | 86 | -4 | 2 | -12 | 4 | 2 | 2 lbs | 5.44 |
| 7:03:56 AM | Screw fan 3 | 32 | -2 | 12 | 22 | 21 | 21 | 2 lbs | 4.23 |
| 7:04:03 AM | Screw fan 4 | -22 | -21 | 21 | -12 | -55 | 12 | 2 lbs | 2.01 |
| 7:04:06 AM | Unknown | 12 | 4 | 2 | 12 | 4 | 2 | | 2.12 |
| 7:04:08 AM | Unknown | 35 | -2 | 12 | 22 | 21 | 21 | | 4.45 |
| 7:04:12 AM | Grab hard-drive | -12 | -21 | 21 | -12 | -55 | 12 | 0.5 lbs | 65.44 |
| 7:04:16 AM | Grab screwdriver | 22 | 4 | 2 | 12 | 4 | 2 | 2 lbs | 26.23 |
| 7:04:22 AM | Grab screws | 32 | -2 | 12 | 22 | 21 | 21 | | 43.01 |
| 7:04:28 AM | Unknown | -2 | -21 | 21 | -12 | -55 | 12 | | 2.12 |
| 7:04:36 AM | Position hard drive | 86 | -4 | 2 | -12 | 4 | 2 | 1 lb | 4.45 |
| 7:04:46 AM | Screw hard drive 1 | 22 | 4 | 2 | 12 | 4 | 2 | 2 lbs | 5.32 |
| 7:04:56 AM | Screw hard drive 2 | 32 | -2 | 12 | 22 | 21 | 21 | 2 lbs | 9.87 |

Accessing information associated with a first actor and second actor, including sensed activity information.

2220

Analyzing the activity information real time, including analyzing activity of the first actor with respect to the second actor.

2230

Forwarding respective feedback in real time based on the results of the analysis to the first actor and the second actor, wherein the feedback includes an indication of a change to first actor or second actor.

FIG. 22

WORKSPACE ACTOR COORDINATION SYSTEMS AND METHODS

CROSS-REFERENCE TO RELATED APPLICATIONS

This application claims the benefit of and priority to U.S. Provisional Patent Application No. 62/581,541 filed Nov. 3, 2017, which is incorporated herein in its entirety.

BACKGROUND

Activities performed in various work environments have made significant contributions toward the advancement of society and to the realization of numerous advantageous results. The manner in which the actors perform the activities typically has significant impact on successfully achieving various objectives associated with the activities. The objectives can include correctly performing an action or task (e.g., assembling product components, interacting with another actor/entity, etc.) effectively and efficiently (e.g., low cost, timely, rapidly, conservation of resources and energy, safely, repeatability, etc.). However, reliable and proper achievement of the various objectives can be difficult.

Numerous factors can impact successful achievement of the objectives. Realization of the objectives can be influenced by the work environment (e.g., manufacturing environments, service environments, medical environments, retail environments, etc.), the nature of the activity itself (e.g., complex, simple, repetitive, non-uniform, safe. hazardous, etc.), and business considerations (e.g., cost, market responsiveness, transportation, etc.). Proper performance of the activities often depends upon the various aspects of actors involved in performing an activity. There can be different actors. An actor can be human, a programmable machine (e.g., a robot, a cobot, a CNC machine, etc.), and a hard automation machine (e.g., a casting machine, a folding machine, etc.). The actors in turn can have various characteristics, attributes, and features. For example, human actors can have intelligence, cognition, instinct, reflex, intuition and so on, but can also be prone to inconsistency, physical limitations, injury and other human limitations. A robot can have precision, repeatability, is untiring, hardy and so on, but lack intuition, intelligence, initiative, adaptability, and so forth. In one embodiment, a programmable machine is relatively difficult and time consuming to program/reprogram and a human is capable of learning and understanding relatively easily and quickly.

Given variances in actor characteristics and capabilities, coordination of actors and activities can have a significant impact on realization of an objective. The types of actors and activities can impact a station or workspace configuration (e.g., layout, space and volume occupied, tooling, etc.), a process output (e.g., capabilities, product quality, etc.), costs (e.g., costs associated with energy utilization, initial investment, labor, tooling, etc.). Conventional attempts at dealing with these numerous complex issues are typically costly and resource intensive, and efficient and effective coordination of actors and activities is traditionally often very problematic or impossible.

SUMMARY

The present technology may best be understood by referring to the following description and accompanying drawings that are used to illustrate embodiments of the present technology directed toward. This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, a method comprises: accessing respective information associated with a first actor and a second actor, including sensed activity information; analyzing the information, including analyzing activity of the first actor with respect to a second actor; and forwarding respective feedback based on the results of the analysis. The feedback can includes an individual objective specific to one of either the first actor or the second actor. The feedback includes collective objective with respect to the first actor or the second actor. The analyzing can include automated artificial intelligence analysis. Sensed activity information can be associated within the activity space, including with a grid. It is appreciated there can be various combinations of actors (e.g., human and device, device and device, human and human, etc.). The feedback can be a configuration layout suggestion. The feedback can be a suggested assignment of a type of actor to an activity.

In one embodiment a system comprises: one or more engines, the one or more engines include: one or more data storage units, the one or more data storage units configured to store information for the engine, including information associated with one or more stations, wherein the one or more stations include a plurality of entities, wherein the plurality of entities includes a first actor and a second actor; one or more engines. The one or more engines can be configured to: access information regarding the one or more stations, including information associated with the first actor, the second actor, and sensed activity information with respect to performing an activity within the station; perform analytics associated with the one or more entities in the station, including analyzing respective activity of the first actor and the second actor; and forward feedback wherein the feedback is based on the results of the analysis. The analyzing can include determination of a work envelope, space utilization, and time/motion determination for both the first actor and the second actor. The analyzing can include utilizing representative and probabilistic models for simulation purposes.

In one exemplary implementation, analyzing includes identification of co-working spaces by overlaying spatial work/task envelope information. A activity space can determined based upon reach, motion, and action data. The analyzing includes utilization of spatio-temporal representations to determine the relative position of the assembly line, the first actor, and the second actor. The analyzing can includes determination of safer parts of a work envelope.

In one embodiment, there are one or more non-transitory computing device-readable storage mediums storing instructions executable by one or more computing devices to perform a method comprising: accessing in real time respective information associated with a first actor and a second actor, including sensed activity information; analyzing the information in real time, including analyzing activity of the first actor with respect to a second actor; and forwarding respective feedback in real time based on the results of the analysis. The accessing can include continually sensing activity associated with the first actor and a second actor. The analyzing can include determining respective activity spaces associated with the first actor and a second actor.

BRIEF DESCRIPTION OF THE DRAWINGS

Embodiments of the present technology are illustrated by way of example and not by way of limitation, in the figures of the accompanying drawings and in which like reference numerals refer to similar elements.

FIG. 11 is a flow chart of an exemplary actor coordination method in accordance with one embodiment.

FIG. 12 is a flow cart of another exemplary actor interaction in accordance with one embodiment.

FIG. 16 is a block diagram of an exemplary data structure in accordance with one embodiment.

FIG. 22 is a flow cart of another exemplary actor interaction method in accordance with one embodiment.

DETAILED DESCRIPTION OF THE INVENTION

Figure 1:
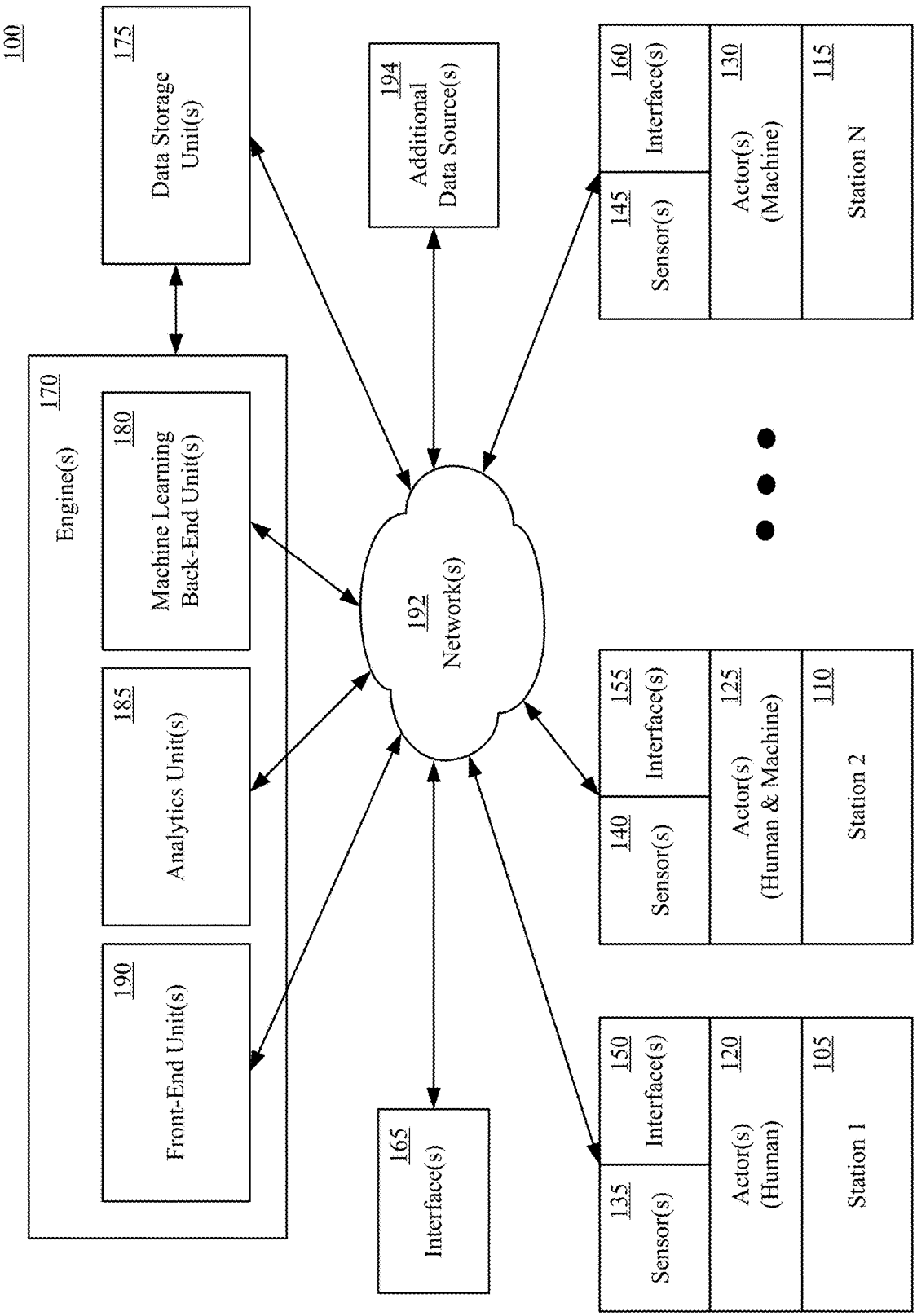
FIG. 1 shows an action recognition and analytics system, in accordance with aspect of the present technology.

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one ordinarily skilled in the art that the present invention may be practiced without these specific details. In other instances, well known methods, procedures, components, and circuits have not been described in detail as not to unnecessarily obscure aspects of the current invention.

As used herein the term process can include processes, procedures, transactions, routines, practices, and the like. As used herein the term sequence can include sequences, orders, arrangements, and the like. As used herein the term action can include actions, steps, tasks, activity, motion, movement, and the like. As used herein the term object can include objects, parts, components, items, elements, pieces, assemblies, sub-assemblies, and the like. As used herein a process can include a set of actions or one or more subsets of actions, arranged in one or more sequences, and performed on one or more objects by one or more actors. As used herein a cycle can include a set of processes or one or more subsets of processes performed in one or more sequences. As used herein a sensor stream can include a video sensor stream, thermal sensor stream, infrared sensor stream, hyperspectral sensor stream, audio sensor stream, depth data stream, and the like. As used herein frame based sensor stream can include any sensor stream that can be represented by a two or more dimensional array of data values. As used herein the term parameter can include parameters, attributes, or the like. As used herein the term indicator can include indicators, identifiers, labels, tags, states, attributes, values or the like. As used herein the term feedback can include feedback, commands, directions, alerts, alarms, instructions, orders, and the like. As used herein the term actor can include actors, workers, employees, operators, assemblers, contractors, associates, managers, users, entities, humans, cobots, robots, and the like as well as combinations of them. As used herein the term robot can include a machine, device, apparatus or the like, especially one programmable by a computer, capable of carrying out a series of actions automatically. The actions can be autonomous, semi-autonomous, assisted, or the like. As used herein the term cobot can include a robot intended to interact with humans in a shared workspace. As used herein the term package can include packages, packets, bundles, boxes, containers, cases, cartons, kits, and the like. As used herein, real time can include responses within a given latency, which can vary from sub-second to seconds.

Referring to FIG. 1 an action recognition and analytics system, in accordance with aspect of the present technology, is shown. The action recognition and analytics system 100 can be deployed in a manufacturing, health care, warehousing, shipping, retail, restaurant or similar context. A manufacturing context, for example, can include one or more stations 105-115 and one or more actors 120-130 disposed at the one or more stations. The actors can include humans, machine or any combination therefore. For example, individual or multiple workers can be deployed at one or more stations along a manufacturing assembly line. One or more robots can be deployed at other stations. A combination of one or more workers and/or one or more robots can be deployed additional stations It is to be noted that the one or more stations 105-115 and the one or more actors are not generally considered to be included in the system 100.

In a health care implementation, an operating room can comprise a single station implementation. A plurality of sensors, such as video cameras, thermal imaging sensors, depth sensors, or the like, can be disposed non-intrusively at various positions around the operating room. One or more additional sensors, such as audio, temperature, acceleration, torque, compression, tension, or the like sensors, can also be disposed non-intrusively at various positions around the operating room.

In a shipping implementation, the plurality of stations may represent different loading docks, conveyor belts, forklifts, sorting stations, holding areas, and the like. A plurality of sensors, such as video cameras, thermal imaging sensors, depth sensors, or the like, can be disposed non-intrusively at various positions around the loading docks, conveyor belts, forklifts, sorting stations, holding areas, and the like. One or more additional sensors, such as audio, temperature, acceleration, torque, compression, tension, or the like sensors, can also be disposed non-intrusively at various positions.

In a retailing implementation, the plurality of stations may represent one or more loading docks, one or more stock rooms, the store shelves, the point of sale (e.g. cashier stands, self-checkout stands and auto-payment geofence), and the like. A plurality of sensors such as video cameras, thermal imaging sensors, depth sensors, or the like, can be disposed non-intrusively at various positions around the loading docks, stock rooms, store shelves, point of sale stands and the like. One or more additional sensors, such as audio, acceleration, torque, compression, tension, or the like sensors, can also be disposed non-intrusively at various positions around the loading docks, stock rooms, store shelves, point of sale stands and the like.

In a warehousing or online retailing implementation, the plurality of stations may represent receiving areas, inventory storage, picking totes, conveyors, packing areas, shipping areas, and the like. A plurality of sensors, such as video cameras, thermal imaging sensors, depth sensors, or the like, can be disposed non-intrusively at various positions around the receiving areas, inventory storage, picking totes, conveyors, packing areas, and shipping areas. One or more additional sensors, such as audio, temperature, acceleration, torque, compression, tension, or the like sensors, can also be disposed non-intrusively at various positions.

Aspect of the present technology will be herein further described with reference to a manufacturing context so as to best explain the principles of the present technology without obscuring aspects of the present technology. However, the present technology as further described below can also be readily applied in health care, warehousing, shipping, retail, restaurants, and numerous other similar contexts.

The action recognition and analytics system 100 can include one or more interfaces 135-165. The one or more interface 135-145 can include one or more sensors 135-145 disposed at the one or more stations 105-115 and configured to capture streams of data concerning cycles, processes, actions, sequences, object, parameters and or the like by the one or more actors 120-130 and or at the station 105-115. The one or more sensors 135-145 can be disposed non-intrusively, so that minimal to changes to the layout of the assembly line or the plant are required, at various positions around one or more of the stations 105-115. The same set of one or more sensors 135-145 can be disposed at each station 105-115, or different sets of one or more sensors 135-145 can be disposed at different stations 105-115. The sensors 135-145 can include one or more sensors such as video cameras, thermal imaging sensors, depth sensors, or the like. The one or more sensors 135-145 can also include one or more other sensors, such as audio, temperature, acceleration, torque, compression, tension, or the like sensors.

The one or more interfaces 135-165 can also include but not limited to one or more displays, touch screens, touch pads, keyboards, pointing devices, button, switches, control panels, actuators, indicator lights, speakers, Augmented Reality (AR) interfaces, Virtual Reality (VR) interfaces, desktop Personal Computers (PCs), laptop PCs, tablet PCs, smart phones, robot interfaces, cobot interfaces. The one or more interfaces 135-165 can be configured to receive inputs from one or more actors 120-130, one or more engines 170 or other entities. Similarly, the one or more interfaces 135-165 can be configured to output to one or more actors 120-130, one or more engine 170 or other entities. For example, the one or more front-end units 190 can output one or more graphical user interfaces to present training content, work charts, real time alerts, feedback and or the like on one or more interfaces 165, such displays at one or more stations 120-130, at management portals on tablet PCs, administrator portals as desktop PCs or the like. In another example, the one or more front-end units 190 can control an actuator to push a defective unit of the assembly line when a defect is detected. The one or more front-end units can also receive responses on a touch screen display device, keyboard, one or more buttons, microphone or the like from one or more actors. Accordingly, the interfaces 135-165 can implement an analysis interface, mentoring interface and or the like of the one or more front-end units 190.

The action recognition and analytics system 100 can also include one or more engines 170 and one or more data storage units 175. The one or more interfaces 135-165, the one or more data storage units 175, the one or more machine learning back-end units 180, the one or more analytics units 185, and the one or more front-end units 190 can be coupled together by one or more networks 192. It is also to be noted that although the above described elements are described as separate elements, one or more elements of the action recognition and analytics system 100 can be combined together or further broken into different elements.

The one or more engines 170 can include one or more machine learning back-end units 180, one or more analytics units 185, and one or more front-end units 190. The one or more data storage units 175, the one or more machine learning back-end units 180, the one or more analytics units 185, and the one or more analytics front-end units 190 can be implemented on a single computing device, a common set of computing devices, separate computing device, or different sets of computing devices that can be distributed across the globe inside and outside an enterprise. Aspects of the one or more machine learning back-end units 180, the one or more analytics units 185 and the one or more front-end units 190, and or other computing units of the action recognition and analytics system 100 can be implemented by one or more central processing units (CPU), one or more graphics processing units (GPU), one or more tensor processing units (TPU), one or more digital signal processors (DSP), one or more microcontrollers, one or more field programmable gate arrays and or the like, and any combination thereof. In addition, the one or more data storage units 175, the one or more machine learning back-end units 180, the one or more analytics units 185, and the one or more front-end units 190 can be implemented locally to the one or more stations 105-115, remotely from the one or more stations 105-115, or any combination of locally and remotely. In one example, the one or more data storage units 175, the one or more machine learning back-end units 180, the one or more analytics units 185, and the one or more front-end units 190 can be implemented on a server local (e.g., on site at the manufacturer) to the one or more stations 105-115. In another example, the one or more machine learning back-end units 135, the one or more storage units 140 and analytics front-end units 145 can be implemented on a cloud computing service remote from the one or more stations 105-115. In yet another example, the one or more data storage units 175 and the one or more machine learning back-end units 180 can be implemented remotely on a server of a vendor, and one or more data storage units 175 and the one or more front-end units 190 are implemented locally on a server or computer of the manufacturer. In other examples, the one or more sensors 135-145, the one or more machine learning back-end units 180, the one or more front-end unit 190, and other computing units of the action recognition and analytics system 100 can perform processing at the edge of the network 192 in an edge computing implementation. The above example of the deployment of one or more computing devices to implement the one or more interfaces 135-165, the one or more engines 170, the one or more data storage units 140 and one or more analytics front-end units 145, are just some of the many different configuration for implementing the one or more machine learning back-end units 135, one or more data storage units 140. Any number of computing devices, deployed locally, remotely, at the edge or the like can be utilized for implementing the one or more machine learning back-end units 135, the one or more data storage units 140, the one or more analytics front-end units 145 or other computing units.

The action recognition and analytics system 100 can also optionally include one or more data compression units associated with one or more of the interfaces 135-165. The data compression units can be configured to compress or decompress data transmitted between the one or more interface 135-165, and the one or more engines 170. Data compression, for example, can advantageously allow the sensor data from the one or more interface 135-165 to be transmitted across one or more existing networks 192 of a manufacturer. The data compression units can also be integral to one or more interfaces 135-165 or implemented separately. For example, video capture sensors may include an integral Motion Picture Expert Group (MPEG) compression unit (e.g., H-264 encoder/decoder). In an exemplary implementation, the one or more data compression units can use differential coding and arithmetic encoding to obtain a 20× reduction in the size of depth data from depth sensors. The data from a video capture sensor can comprise roughly 30 GB of H.264 compressed data per camera, per day for a factory operation with three eight-hour shifts. The depth data can comprise roughly another 400 GB of uncompressed data per sensor, per day. The depth data can be compressed by an algorithm to approximately 20 GB per sensor, per day. Together, a set of a video sensor and a depth sensor can generate approximately 50 GB of compressed data per day. The compression can allow the action recognition and analytics system 100 to use a factory's network 192 to move and store data locally or remotely (e.g., cloud storage).

The action recognition and analytics system 100 can also be communicatively coupled to additional data sources 194, such as but not limited to a Manufacturing Execution Systems (MES), warehouse management system, or patient management system. The action recognition and analytics system 100 can receive additional data, including one or more additional sensor streams, from the additional data sources 194. The action recognition and analytics system 100 can also output data, sensor streams, analytics result and or the like to the additional data sources 194. For example, the action recognition can identify a barcode on an object and provide the barcode input to a MES for tracking.

The action recognition and analytics system 100 can continually measure aspects of the real-world, making it possible to describe a context utilizing vastly more detailed data sets, and to solve important business problems like line balancing, ergonomics, and or the like. The data can also reflect variations over time. The one or more machine learning back-end units 170 can be configured to recognize, in real time, one or more cycles, processes, actions, sequences, objects, parameters and the like in the sensor streams received from the plurality of sensors 135-145. The one or more machine learning back-end units 180 can recognize cycles, processes, actions, sequences, objects, parameters and the like in sensor streams utilizing deep learning, decision tree learning, inductive logic programming, clustering, reinforcement learning, Bayesian networks, and or the like.

Figure 2:
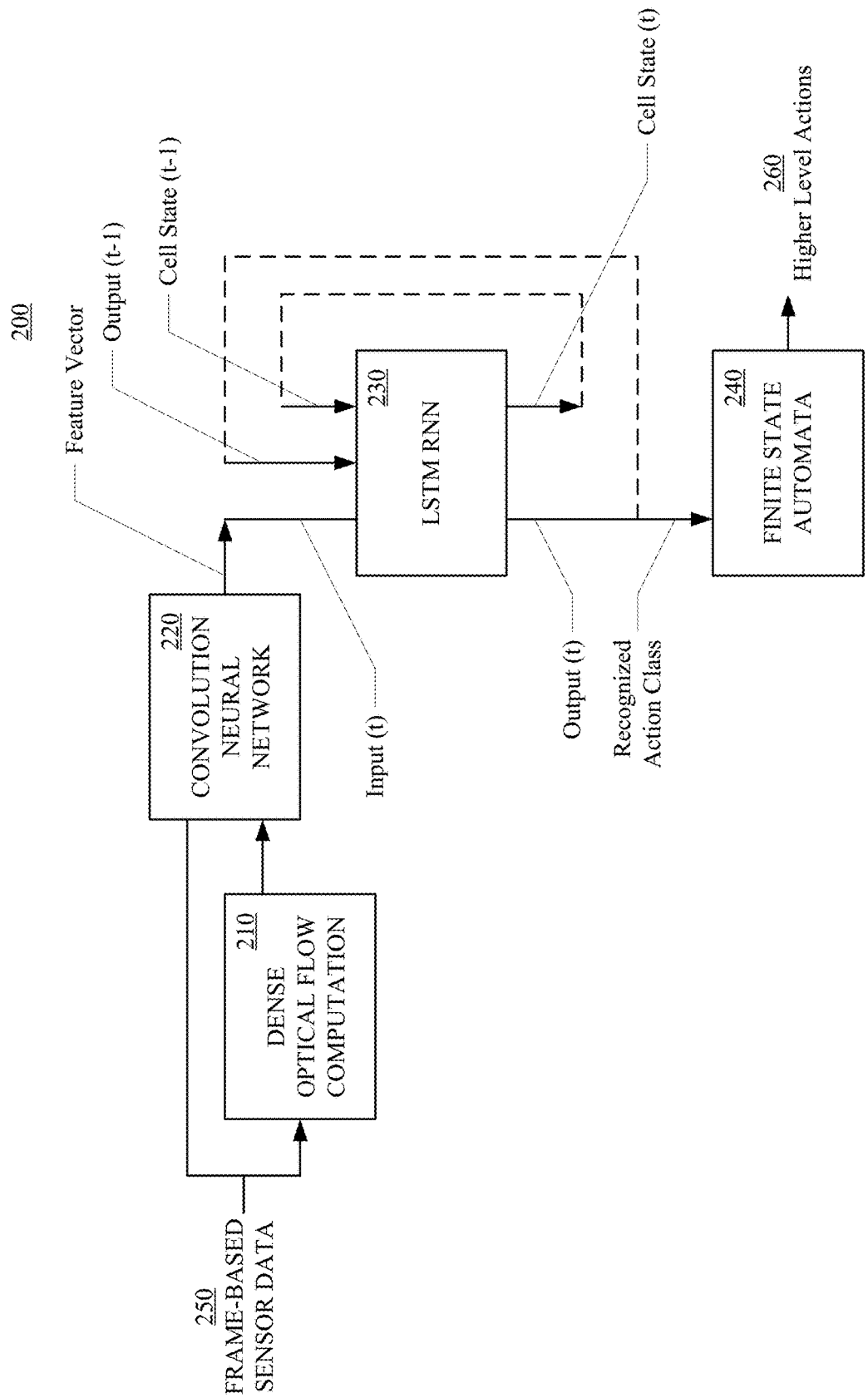
FIG. 2 shows an exemplary deep learning type machine learning back-end unit, in accordance with aspects of the present technology.

Referring now to FIG. 2, an exemplary deep learning type machine learning back-end unit, in accordance with aspects of the present technology, is shown. The deep learning unit 200 can be configured to recognize, in real time, one or more cycles, processes, actions, sequences, objects, parameters and the like in the sensor streams received from the plurality of sensors 120-130. The deep learning unit 200 can include a dense optical flow computation unit 210, a Convolution Neural Networks (CNNs) 220, a Long Short Term Memory (LSTM) Recurrent Neural Network (RNN) 230, and a Finite State Automata (FSA) 240. The CNNs 220 can be based on two-dimensional (2D) or three-dimensional (3D) convolutions. The dense optical flow computation unit 210 can be configured to receive a stream of frame-based sensor data 250 from sensors 120-130. The dense optical flow computation unit 210 can be configured to estimate an optical flow, which is a two-dimension (2D) vector field where each vector is a displacement vector showing the movement of points from a first frame to a second frame. The CNNs 220 can receive the stream of frame-based sensor data 250 and the optical flow estimated by the dense optical flow computation unit 210. The CNNs 220 can be applied to video frames to create a digest of the frames. The digest of the frames can also be referred to as the embedding vector. The digest retains those aspects of the frame that help in identifying actions, such as the core visual clues that are common to instances of the action in question.

In a three-dimensional Convolution Neural Network (3D CNN) based approach, spatio-temporal convolutions can be performed to digest multiple video frames together to recognize actions. For 3D CNN, the first two dimension can be along space, and in particular the width and height of each video frame. The third dimension can be along time. The neural network can learn to recognize actions not just from the spatial pattern in individual frame, but also jointly in space and time. The neural network is not just using color patterns in one frame to recognize actions. Instead, the neural network is using how the pattern shifts with time (i.e., motion cues) to come up with its classification. According the 3D CNN is attention driven, in that it proceeds by identifying 3D spatio-temporal bounding boxes as Regions of Interest (RoI) and focusses on them to classify actions.

In one implementation, the input to the deep learning unit 200 can include multiple data streams. In one instance, a video sensor signal, which includes red, green and blue data streams, can comprise three channels. Depth image data can comprise another channel. Additional channels can accrue from temperature, sound, vibration, data from sensors (e.g., torque from a screwdriver) and the like. From the RGB and depth streams, dense optical flow fields can be computed by the dense optical flow computation unit 210 and fed to the Convolution Neural Networks (CNNs) 220. The RGB and depth streams can also be fed to the CNNs 220 as additional streams of derived data.

The Long Short Term Memory (LSTM) Recurrent Neural Network (RNN) 230 can be fed the digests from the output of the Convolution Neural Networks (CNNs) 220. The LSTM can essentially be a sequence identifier that is trained to recognize temporal sequences of sub-events that constitute an action. The combination of the CNNs and LSTM can be jointly trained, with full back-propagation, to recognize low-level actions. The low-level actions can be referred to as atomic actions, like picking a screw, picking a screwdriver, attaching screw to screwdriver and the like. The Finite State Automata (FSA) 240 can be mathematical models of computations that include a set of state and a set of rules that govern the transition between the states based on the provided input. The FSA 240 can be configured to recognize higher-level actions 260 from the atomic actions. The high-level actions 260 can be referred to as molecular actions, for example turning a screw to affix a hard drive to a computer chassis. The CNNs and LSTM can be configured to perform supervised training on the data from the multiple sensor streams. In one implementation, approximately 12 hours of data, collected over the course of several days, can be utilized to train the CNNs and LSTM combination.

Figure 3:
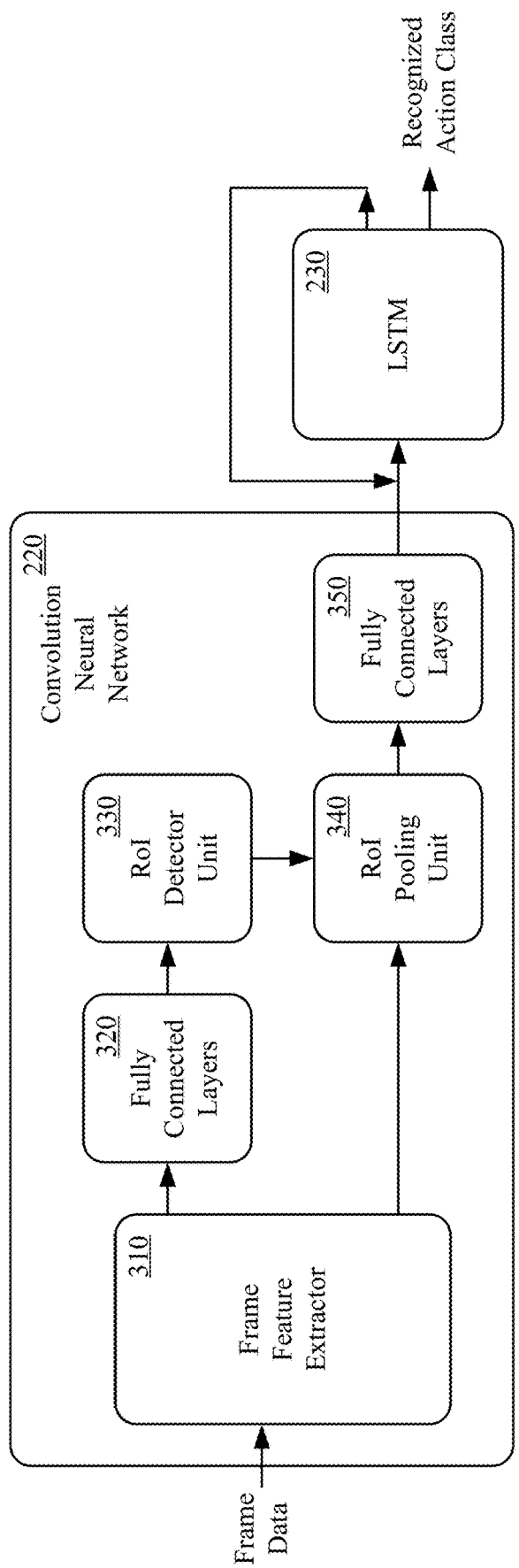
FIG. 3 shows an exemplary Convolution Neural Network (CNN) and Long Short Term Memory (LSTM) Recurrent Neural Network (RNN), in accordance with aspects of the present technology.
Figure 4:
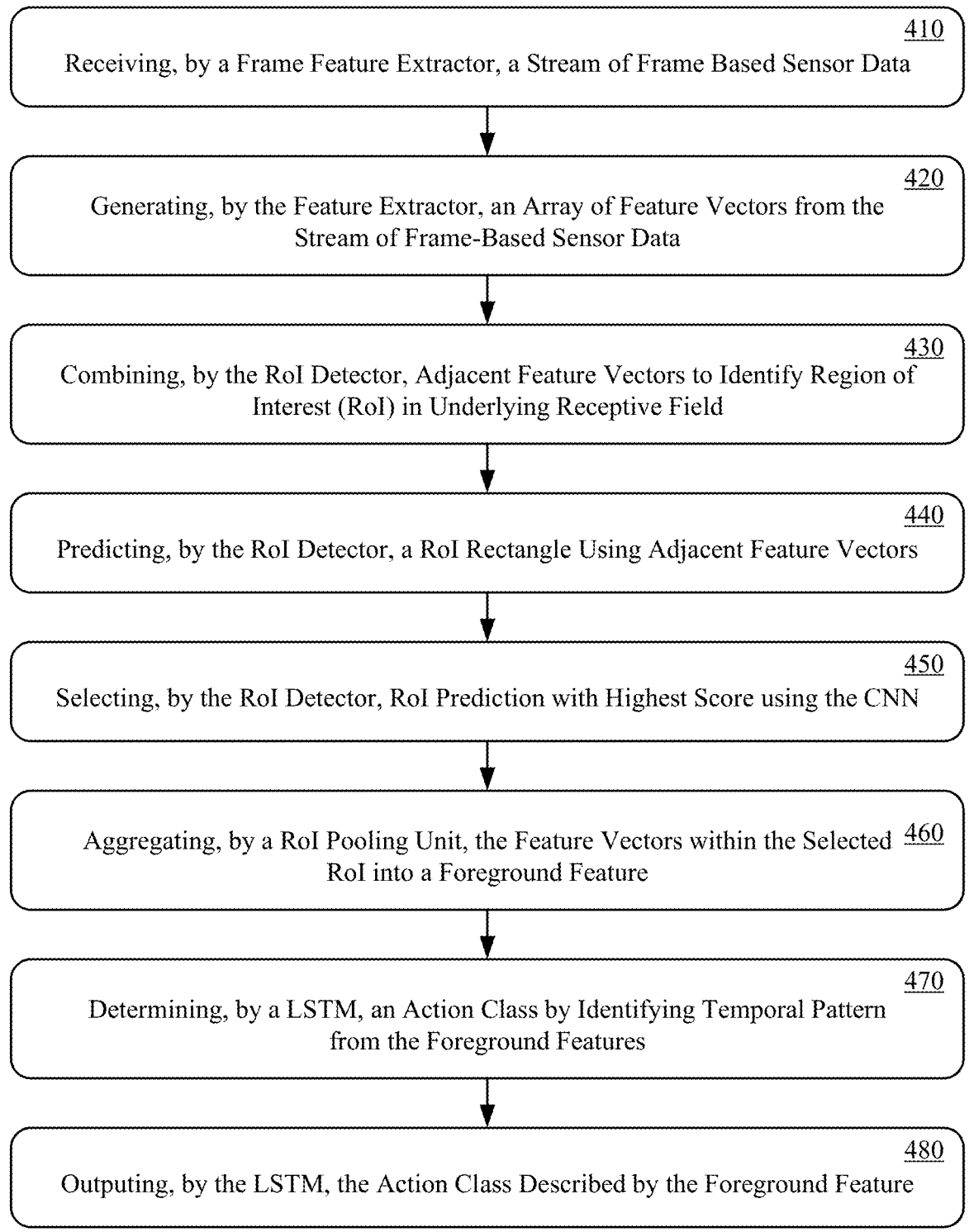
FIG. 4 shows an exemplary method of detecting actions in a sensor stream, in accordance with aspects of the present technology.

Referring now to FIG. 3, an exemplary Convolution Neural Networks (CNNs) and Long Short Term Memory (LSTM) Recurrent Neural Network (RNN), in accordance with aspects of the present technology, is shown. The CNNs can include a frame feature extractor 310, a first Fully Connected (FC) layer 320, a Region of Interest (RoI) detector unit 330, a RoI pooling unit 340, and a second Fully Connected (FC) layer 350. The operation of the CNNs and LSTM will be further explained with reference to FIG. 4, which shows an exemplary method of detecting actions in a sensor stream.

The frame feature extractor 310 of the Convolution Neural Networks (CNNs) 220 can receive a stream of frame-based sensor data, at 410. At 420, the frame feature extractor 310 can perform a two-dimensional convolution operation on the received video frame and generate a two-dimensional array of feature vectors. The frame feature extractor 310 can work on the full resolution image, wherein a deep network is effectively sliding across the image generating a feature vector at each stride position. Thus, each element of the 2D feature vector array is a descriptor for the corresponding receptive field (e.g., fixed portion of the underlying image). The first Fully Connected (FC) layer can flatten the high-level features extracted by the frame feature extractor 310, and provide additional non-linearity and expressive power, enabling the machine to learn complex non-linear combinations of these features.

At 430, the RoI detector unit 330 can combine neighboring feature vectors to make a decision on whether the underlying receptive field belongs to a Region of Interest (RoI) or not. If the underlying receptive field belongs to a RoI, a RoI rectangle can be predicted from the same set of neighboring feature vectors, at 440. At, 450, a RoI rectangle with a highest score can be chosen by the RoI detector unit 330. For the chosen RoI rectangle, the feature vectors lying within it can be aggregated by the RoI pooling unit 340, at 460. The aggregated feature vector is a digest/descriptor for the foreground for that video frame.

In one implementation, the RoI detector unit 330 can determine a static RoI. The static RoI identifies a Region of Interest (RoI) within an aggregate set of feature vectors describing a video frame, and generates a RoI area for the identified RoI. A RoI area within a video frame can be indicated with a RoI rectangle that encompasses an area of the video frame designated for action recognition, such as an area in which actions are performed in a process. Alternatively, the RoI area can be designated with a box, circle, highlighted screen, or any other geometric shape or indicator having various scales and aspect ratios used to encompass a RoI. The area within the RoI rectangle is the area within the video frame to be processed by the Long Short Term Memory (LSTM) for action recognition.

The Long Short Term Memory (LSTM) can be trained using a RoI rectangle that provides, both, adequate spatial context within the video frame to recognize actions and independence from irrelevant portions of the video frame in the background. The trade-off between spatial context and background independence ensures that the static RoI detector can provide clues for the action recognition while avoiding spurious unreliable signals within a given video frame.

In another implementation, the RoI detector unit 330 can determine a dynamic RoI. A RoI rectangle can encompass areas within a video frame in which an action is occurring. By focusing on areas in which action occurs, the dynamic RoI detector enables recognition of actions outside of a static RoI rectangle while relying on a smaller spatial context, or local context, than that used to recognize actions in a static RoI rectangle.

In one implementation, the RoI pooling unit 340 extracts a fixed-sized feature vector from the area within an identified RoI rectangle, and discards the remaining feature vectors of the input video frame. The fixed-sized feature vector, or foreground feature, includes the feature vectors generated by the video frame feature extractor that are located within the coordinates indicating a RoI rectangle as determined by the RoI detector unit 330. Because the RoI pooling unit 340 discards feature vectors not included within the RoI rectangle, the Convolution Neural Networks (CNNs) 220 analyzes actions within the RoI only, thus ensuring that unexpected changes in the background of a video frame are not erroneously analyzed for action recognition.

In one implementation, the Convolution Neural Networks (CNNs) 220 can be an Inception ResNet. The Inception ResNet can utilize a sliding window style operation. Successive convolution layers output a feature vector at each point of a two-dimensional grid. The feature vector at location (x,y) at level 1 can be derived by weighted averaging features from a small local neighborhood (aka receptive field) N around the (x,y) at level 1-1 followed by a pointwise non-linear operator. The non-linear operator can be the RELU (max(0,x)) operator.

In the sliding window, there can be many more than 7×7 points at the output of the last convolution layer. A Fully Connected (FC) convolution can be taken over the feature vectors from the 7×7 neighborhoods, which is nothing but applying one more convolution. The corresponding output represents the Convolution Neural Networks (CNNs) output at the matching 224×224 receptive field on the input image. This is fundamentally equivalent to applying the CNNs to each sliding window stop. However, no computation is repeated, thus keeping the inferencing computation cost real time on Graphics Processing Unit (GPU) based machines.

The convolution layers can be shared between RoI detector 330 and the video frame feature extractor 310. The RoI detector unit 330 can identify the class independent rectangular region of interest from the video frame. The video frame feature extractor can digest the video frame into feature vectors. The sharing of the convolution layers improves efficiency, wherein these expensive layers can be run once per frame and the results saved and reused.

One of the outputs of the Convolution Neural Networks (CNNs) is the static rectangular Region of Interest (RoI). The term "static" as used herein denotes that the RoI does not vary greatly from frame to frame, except when a scene change occurs, and it is also independent of the output class.

A set of concentric anchor boxes can be employed at each sliding window stop. In one implementation, there can be nine anchor boxes per sliding window stop for combinations of 3 scales and 3 aspect ratios. Therefore, at each sliding window stop there are two set of outputs. The first set of outputs can be a Region of Interest (RoI) present/absent that includes 18 outputs of the form 0 or 1. An output of 0 indicates the absence of a RoI within the anchor box, and an output of 1 indicates the presence of a RoI within the anchor box. The second set of outputs can include Bounding Box (BBox) coordinates including 36 floating point outputs indicating the actual BBox for each of the 9 anchor boxes. The BBox coordinates are to be ignored if the RoI present/absent output indicates the absence of a RoI.

For training, sets of video frames with a per-frame Region of Interest (RoI) rectangle are presented to the network. In frames without a RoI rectangle, a dummy 0×0 rectangle can be presented. The Ground Truth for individual anchor boxes can be created via the Intersection over Union (IoU) of rectangles. For the ith anchor box $\vec{b_i}=\{x_i, y_i, w_i, h_i\}$ the derived Ground Truth for the RoI presence probability can be determined by Equation 1:

$$p_i^* = \begin{cases} 1 & IoU(\vec{b_i}, \vec{g}) >= 0.7 \\ 0 & IoU(\vec{b_i}, \vec{g}) <= 0.1 \\ \text{box unused for training} \end{cases}$$

where $\vec{g}=\{x_g, y_g, w_g, h_g\}$ is the Ground Truth RoI box for the entire frame.

The loss function can be determined by Equation 2:

$$L(p_i, p_i^*, \vec{b_i}, \vec{g}) = \sum_n p_i^* \log p_i (S(x_i - x_g) + S(y_i - y_g) + S(w_i - w_g) + S(h_i - h_g))$$

where pi is the predicted probability for presence of Region of Interest (RoI) in the ith anchor box and the smooth loss function can be defined by Equation 3:

$$S(x) = \begin{cases} 0.5x^2 & |x| < 1 \\ |x| - 0.5 & \text{otherwise} \end{cases}$$

The left term in the loss function is the error in predicting the probability of the presence of a RoI, while the second term is the mismatch in the predicted Bounding Box (BBox). It should be noted that the second term vanishes when the ground truth indicates that there is no RoI in the anchor box.

The static Region of Interest (RoI) is independent of the action class. In another implementation, a dynamic Region of Interest (RoI), that is class dependent, is proposed by the CNNs. This takes the form of a rectangle enclosing the part of the image where the specific action is occurring. This increases the focus of the network and takes it a step closer to a local context-based action recognition.

Once a Region of Interest (RoI) has been identified, the frame feature can be extracted from within the RoI. These will yield a background independent frame digest. But this feature vector also needs to be a fixed size so that it can be fed into the Long Short Term Memory (LSTM). The fixed size can be achieved via RoI pooling. For RoI pooling, the RoI can be tiled up into 7×7 boxes. The mean of all feature vectors within a tile can then be determined. Thus, 49 feature vectors that are concatenated from the frame digest can be produced. The second Fully Connected (FC) layer 350 can provide additional non-linearity and expressive power to the machine, creating a fixed size frame digest that can be consumed by the LSTM 230.

At 470, successive foreground features can be fed into the Long Short Term Memory (LSTM) 230 to learn the temporal pattern. The LSTM 230 can be configured to recognize patterns in an input sequence. In video action recognition, there could be patterns within sequences of frames belonging to a single action, referred to as intra action patterns. There could also be patterns within sequences of actions, referred to as inter action patterns. The LSTM can be configured to learn both of these patterns, jointly referred to as temporal patterns. The Long Short Term Memory (LSTM) analyzes a series of foreground features to recognize actions belonging to an overall sequence. In one implementation, the LSTM outputs an action class describing a recognized action associated with an overall process for each input it receives. In another implementation, each class action is comprised of sets of actions describing actions associated with completing an overall process. Each action within the set of actions can be assigned a score indicating a likelihood that the action matches the action captured in the input video frame. Each action may be assigned a score such that the action with the highest score is designated the recognized action class.

Foreground features from successive frames can be feed into the Long Short Term Memory (LSTM). The foreground feature refers to the aggregated feature vectors from within the Region of Interest (RoI) rectangles. The output of the LSTM at each time step is the recognized action class. The loss for each individual frame is the cross entropy softmax loss over the set of possible action classes. A batch is defined as a set of three randomly selected set of twelve frame sequences in the video stream. The loss for a batch is defined as the frame loss averaged over the frame in the batch. The numbers twelve and three are chose empirically. The overall LSTM loss function is given by Equation 4:

$$L(B_1\{S_1, S_2, \ldots, S_{\|B\|}\}) = \sum_{k=1}^{\|B\|} \sum_{t=1}^{\|S\|} \sum_{i=1}^{\|A\|} -\left(\frac{a^{*ti}}{\sum_{j=1}^{\|d\|} a_{t_{i_j}}}\right) \log a_{t_i}^*$$

where B denotes a batch of $\|B\|$ frame sequences $\{S_1, S_2, \ldots, S_{\|B\|}\}$. $S_k$ comprises a sequence of $\|S_k\|$ frames, wherein in the present implementation $\|B\|=3$ and $\|S_k\|=12$ k. A denotes the set of all action classes, $a_{t_i}$ denotes the ith action class score for the tth frame from LSTM and $a_{t_i}^*$ denotes the corresponding Ground Truth.

Referring again to FIG. 1, the machine learning back-end unit 135 can utilize custom labelling tools with interfaces optimized for labeling RoI, cycles and action. The labelling tools can include both standalone application built on top of Open source Computer Vision (OpenCV) and web browser application that allow for the labeling of video segment.

Figure 5:
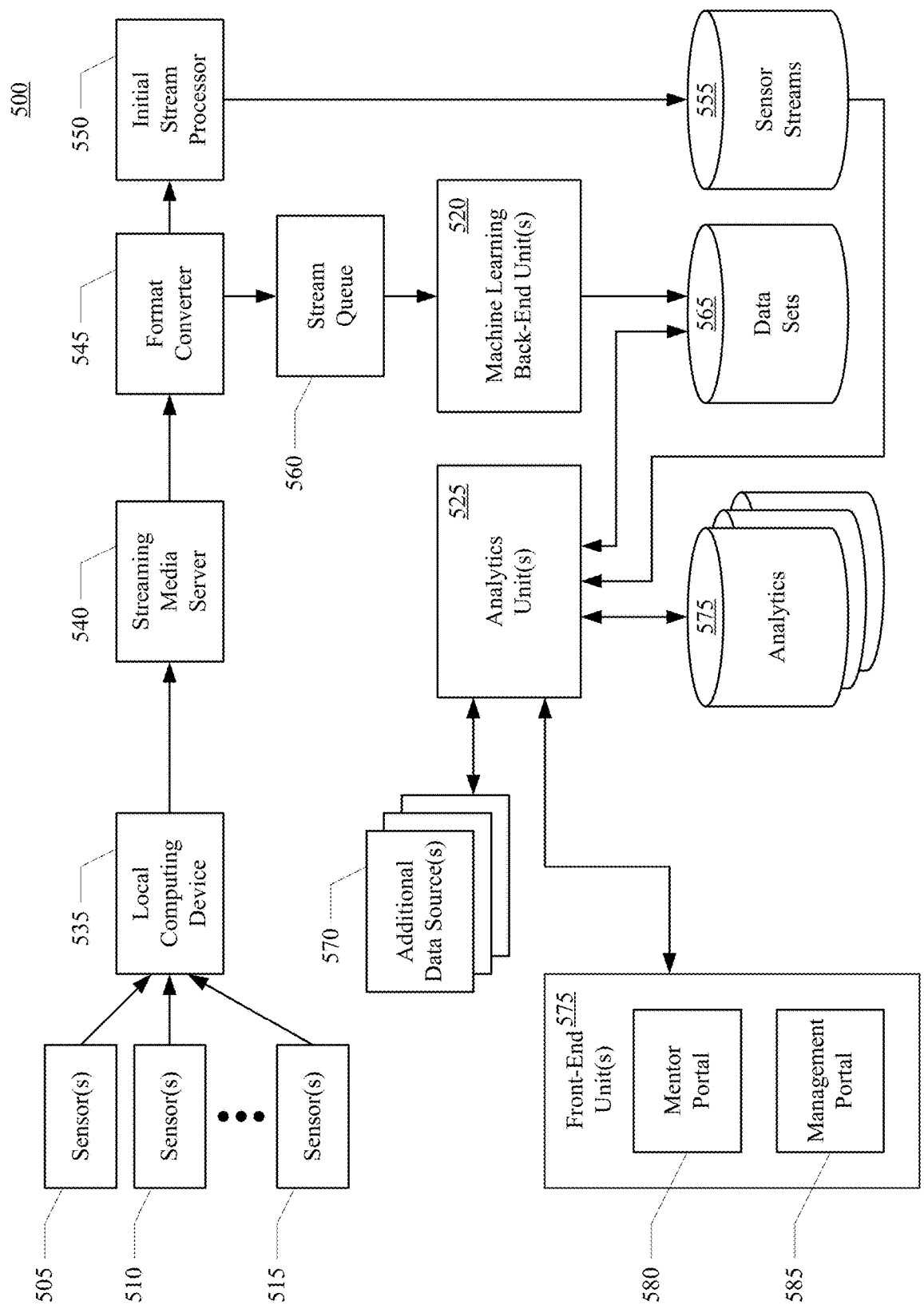
FIG. 5 shows an action recognition and analytics system, in accordance with aspects of the present technology.

Referring now to FIG. 5, an action recognition and analytics system, in accordance with aspect of the present technology, is shown. Again, the action recognition and analytics system 500 can be deployed in a manufacturing, health care, warehousing, shipping, retail, restaurant, or similar context. The system 500 similarly includes one or more sensors 505-515 disposed at one or more stations, one or more machine learning back-end units 520, one or more analytics units 525, and one or more front-end units 530. The one or more sensors 505-515 can be coupled to one or more local computing devices 535 configured to aggregate the sensor data streams from the one or more sensors 505-515 for transmission across one or more communication links to a streaming media server 540. The streaming media server 540 can be configured to received one or more streams of sensor data from the one or more sensors 505-515. A format converter 545 can be coupled to the streaming media server 540 to receive the one or more sensor data streams and convert the sensor data from one format to another. For example, the one or more sensors may generate Motion Picture Expert Group (MPEG) formatted (e.g., H.264) video sensor data, and the format converter 545 can be configured to extract frames of JPEG sensor data. An initial stream processor 550 can be coupled to the format convert 555. The initial stream processor 550 can be configured to segment the sensor data into pre-determined chucks, subdivide the chunks into key frame aligned segment, and create per segment sensor data in one or more formats. For example, the initial stream processor 550 can divide the sensor data into five minute chunks, subdivide the chunks into key frame aligned segment, and convert the key frame aligned segments into MPEG, MPEG Dynamic Adaptive Streaming over Hypertext Transfer Protocol (DASH) format, and or the like. The initial stream processor 550 can be configured to store the sensor stream segments in one or more data structures for storing sensor streams 555. In one implementation, as sensor stream segments are received, each new segment can be appended to the previous sensor stream segments stored in the one or more data structures for storing sensor streams 555.

Figure 6:
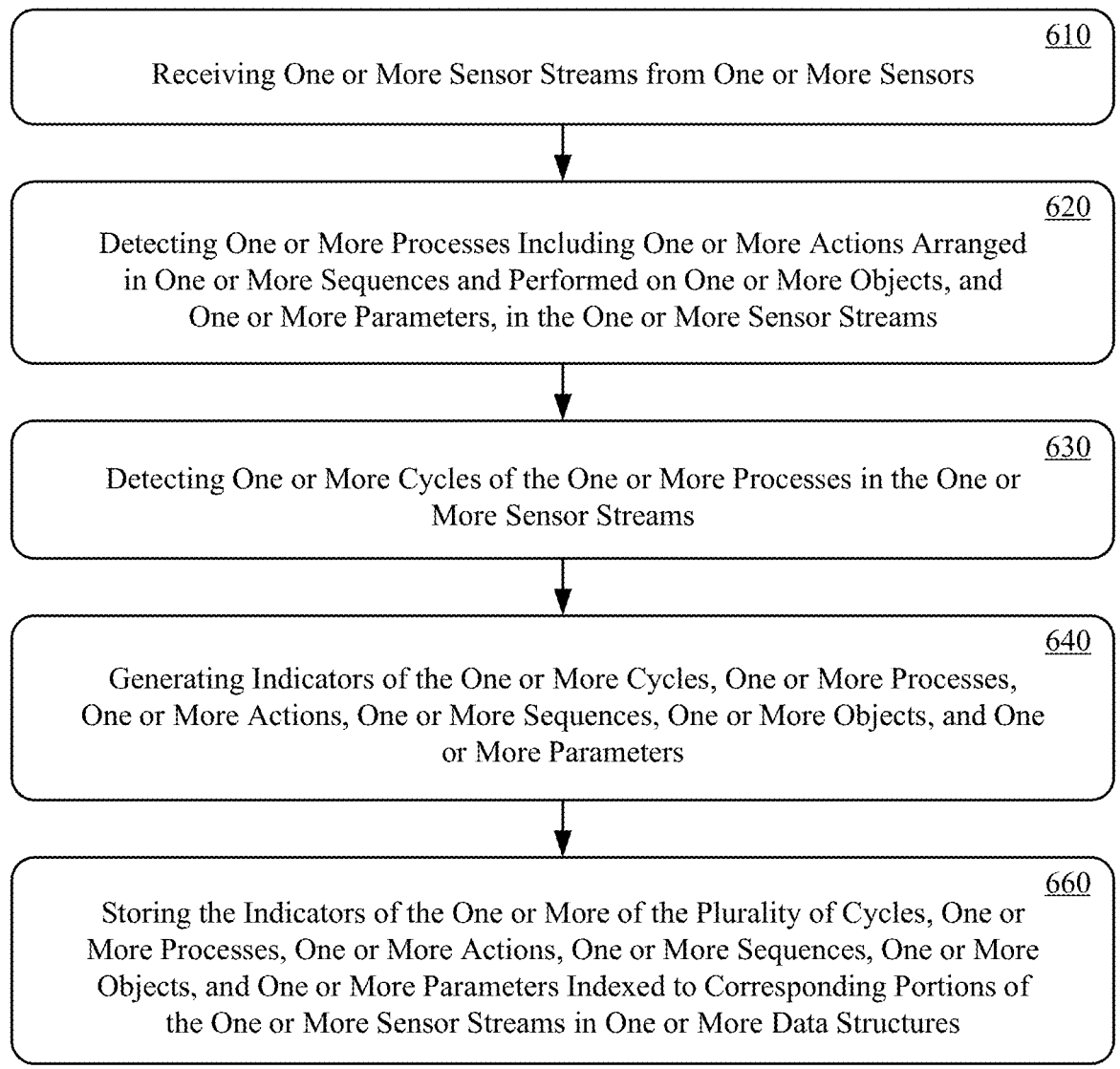
FIG. 6 shows an exemplary method of detecting actions, in accordance with aspects of the present technology.

A stream queue 560 can also be coupled to the format converter 545. The stream queue 560 can be configured to buffer the sensor data from the format converter 545 for processing by the one or more machine learning back-end units 520. The one or more machine learning back-end units 520 can be configured to recognize, in real time, one or more cycles, processes, actions, sequences, objects, parameters and the like in the sensor streams received from the plurality of sensors 505-515. Referring now to FIG. 6, an exemplary method of detecting actions, in accordance with aspects of the present technology, is shown. The action recognition method can include receiving one or more sensor streams from one or more sensors, at 610. In one implementation, one or more machine learning back-end units 520 can be configured to receive sensor streams from sensors 505-515 disposed at one or more stations.

At 620, a plurality of processes including one or more actions arranged in one or more sequences and performed on one or more objects, and one or more parameters can be detected. in the one or more sensor streams. At 630, one or more cycles of the plurality of processes in the sensor stream can also be determined. In one implementation, the one or more machine learning back-end units 520 can recognize cycles, processes, actions, sequences, objects, parameters and the like in sensor streams utilizing deep learning, decision tree learning, inductive logic programming, clustering, reinforcement learning, Bayesian networks, and or the like.

At 640, indicators of the one or more cycles, one or more processes, one or more actions, one or more sequences, one or more objects, and one or more parameters can be generated. In one implementation, the one or more machine learning back-end units 520 can be configured to generate indicators of the one or more cycles, processes, actions, sequences, objects, parameters and or the like. The indicators can include descriptions, identifiers, values and or the like associated with the cycles, processes, actions, sequences, objects, and or parameters. The parameters can include, but is not limited to, time, duration, location (e.g., x, y, z, t), reach point, motion path, grid point, quantity, sensor identifier, station identifier, and bar codes.

At 650, the indicators of the one or more cycles, one or more processes, one or more actions, one or more sequences, one or more objects, and one or more parameters indexed to corresponding portions of the sensor streams can be stored in one or more data structures for storing data sets 565. In one implementation, the one or more machine learning back-end units 520 can be configured to store a data set including the indicators of the one or more processes, one or more actions, one or more sequences, one or more objects, and one or more parameters for each cycle. The data sets can be stored in one or more data structures for storing the data sets 565. The indicators of the one or more cycles, one or more processes, one or more actions, one or more sequences, one or more objects, and one or more parameters in the data sets can be indexed to corresponding portion of the sensor streams in one or more data structures for storing sensor streams 555.

In one implementation, the one or more streams of sensor data and the indicators of the one or more of the plurality of cycles, one or more processes, one or more actions, one or more sequences, one or more objects and one or more parameters indexed to corresponding portion of the one or more streams of sensor data can be encrypted when stored to protect the integrity of the streams of sensor data and or the data sets. In one implementation, the one or more streams of sensor data and the indicators of the one or more of the plurality of cycles, one or more processes, one or more actions, one or more sequences, one or more objects and one or more parameters indexed to corresponding portion of the one or more streams of sensor data can be stored utilizing block chaining. The blockchaining can be applied across the cycles, sensor streams, stations, supply chain and or the like. The blockchaining can include calculating a cryptographic hash based on blocks of the data sets and or blocks of the streams of sensor data. The data sets, streams of sensor data and the cryptographic hash can be stored in one or more data structures in a distributed network.

Referring again to FIG. 5, the one or more analytics units 525 can be coupled to the one or more data structures for storing the sensor streams 555, one or more data structures for storing the data set 565, one or more additional sources of data 570, one or more data structures for storing analytics 575. The one or more analytics units 525 can be configured to perform statistical analysis on the cycle, process, action, sequence, object and parameter data in one or more data sets. The one or more analytics units 525 can also utilize additional data received from one or more additional data sources 570. The additional data sources 570 can include, but are not limited to, Manufacturing Execution Systems (MES), warehouse management system, or patient management system, accounting systems, robot datasheets, human resource records, bill of materials, and sales systems. Some examples of data that can be received from the additional data sources 570 can include, but is not limited to, time, date, shift, day of week, plant, factory, assembly line, sub-assembly line, building, room, supplier, work space, action capability, and energy consumption, ownership cost. The one or more analytics units 525 can be configured to utilize the additional data from one or more additional source of data 570 to update, correct, extend, augment or the like, the data about the cycles, processes, action, sequences, objects and parameters in the data sets. Similarly, the additional data can also be utilized to update, correct, extend, augment or the like, the analytics generate by the one or more analytics front-end units 525. The one or more analytics units 525 can also store trends and other comparative analytics utilizing the data sets and or the additional data, can use sensor fusion to merge data from multiple sensors, and other similar processing and store the results in the one or more data structures for storing analytics 575. In one implementation, one or more engines 170, such as the one or more machine learning back-end units 520 and or the one or more analytics units 525, can create a data structure including a plurality of data sets, the data sets including one or more indicators of at least one of one or more cycles, one or more processes, one or more actions, one or more sequences, one or more object and one or more parameters. The one or more engine 170 can build the data structure based on the one of one or more cycles, one or more processes, one or more actions, one or more sequences, one or more object and one or more parameters detected in the one or more sensor streams. The data structure definition, configuration and population can be performed in real time based upon the content of the one or more sensor streams. For example, Table 1 shows a table defined, configured and populated as the sensor streams are processed by the one or more machine learning back-end unit 520.

TABLE 1

ENTITY ID DATA STUCTURE (TABLE 1)

| FRAME | HUMAN | HAND | ARM | LEG | MOTHER-BOARD | SCREW |
|---|---|---|---|---|---|---|
| 1 | Yes | Yes | Yes | Yes | YES | Yes |
| 2 | Yes | No | No | Yes | Yes | No |
| 3 | Yes | Yes | Yes | Yes | YES | Yes |

The data structure creation process can continue to expand upon the initial structure and or create additional data structures base upon additional processing of the one or more sensor streams.

In one embodiment, the status associated with entities is added to a data structure configuration (e.g., engaged in an action, subject to a force, etc.) based upon processing of the access information. In one embodiment, activity associated with the entities is added to a data structure configuration (e.g., engaged in an action, subject to a force, etc.) based upon processing of the access information. One example of entity status data set created from processing of above entity ID data set (e.g., motion vector analysis of image object, etc.) is illustrated in Table 2.

TABLE 2

ENTITY STATUS DATA STRUCTURE (TABLE 2)

| FRAME | HAND MOVING | ARM MOVING | LEG MOVING | HUMAN MOVING |
|---|---|---|---|---|
| 1 | Yes | Yes | No | Yes |
| 2 | No | No | Yes | No |
| 3 | Yes | Yes | Yes | Yes |

In one embodiment, a third-party data structure as illustrated in Table 3 can be accessed.

TABLE 3

OSHA DATA STRUCTURE (TABLE 3)

| ACTIVITY | SAFE TO MOVE LEG | SAFE TO MOVE HAND |
|---|---|---|
| SCREWING TO MOTHERBOARD | No | Yes |
| LIFTING HOUSING | Yes | Yes |

In one embodiment, activity associated with entities is added to a data structure configuration (e.g., engaged in an action, subject to a force, etc.) based upon processing of the access information as illustrated in Table 4.

TABLE 4

ACTIVITY DATA STRUCTURE (TABLE 4)

| FRAME | SCREWING TO MOTHERBOARD | HUMAN ACTION SAFE | MOTHERBOARD COMPLETE |
|---|---|---|---|
| 1 | Yes | Yes | Yes |
| 2 | No | NA | NO |
| 3 | Yes | NO | Yes |

Table 4 is created by one or more engines 170 based on further analytics/processing of info in Table 1, Table 2 and Table 3. In one example, Table 4 is automatically configured to have a column for screwing to motherboard. In frames 1 and 3 since hand is moving (see Table 2) and screw present (see Table 1), then screwing to motherboard (see Table 3). In frame 2, since hand is not moving (see Table 2) and screw not present (see Table 1), then no screwing to motherboard (see Table 3).

Table 4 is also automatically configured to have a column for human action safe. In frame 1 since leg not moving in frame (see Table 2) the worker is safely (see Table 3) standing at workstation while engage in activity of screwing to motherboard. In frame 3 since leg moving (see Table 2) the worker is not safely (see Table 3) standing at workstation while engage in activity of screwing to motherboard.

The one or more analytics units 525 can also be coupled to one or more front-end units 580. The one or more front-end units 575 can include a mentor portal 580, a management portal 585, and other similar portals. The mentor portal 550 can be configured for presenting feedback generated by the one or more analytics units 525 and or the one or more front-end units 575 to one or more actors. For example, the mentor portal 580 can include a touch screen display for indicating discrepancies in the processes, actions, sequences, objects and parameters at a corresponding station. The mentor portal 580 could also present training content generated by the one or more analytics units 525 and or the one or more front-end units 575 to an actor at a corresponding station. The management port 585 can be configured to enable searching of the one or more data structures storing analytics, data sets and sensor streams. The management port 585 can also be utilized to control operation of the one or more analytics units 525 for such functions as generating training content, creating work charts, performing line balancing analysis, assessing ergonomics, creating job assignments, performing causal analysis, automation analysis, presenting aggregated statistics, and the like.

The action recognition and analytics system 500 can non-intrusively digitize processes, actions, sequences, objects, parameters and the like performed by numerous entities, including both humans and machines, using machine learning. The action recognition and analytics system 500 enables human activity to be measured automatically, continuously and at scale. By digitizing the performed processes, actions, sequences, objects, parameters, and the like, the action recognition and analytics system 500 can optimize manual and/or automatic processes. In one instance, the action recognition and analytics system 500 enables the creation of a fundamentally new data set of human activity. In another instance, the action recognition and analytics system 500 enables the creation of a second fundamentally new data set of man and machine collaborating in activities. The data set from the action recognition and analytics system 500 includes quantitative data, such as which actions were performed by which person, at which station, on which specific part, at what time. The data set can also include judgements based on performance data, such as does a given person perform better or worse that average. The data set can also include inferences based on an understanding of the process, such as did a given product exited the assembly line with one or more incomplete tasks.

Figure 7:
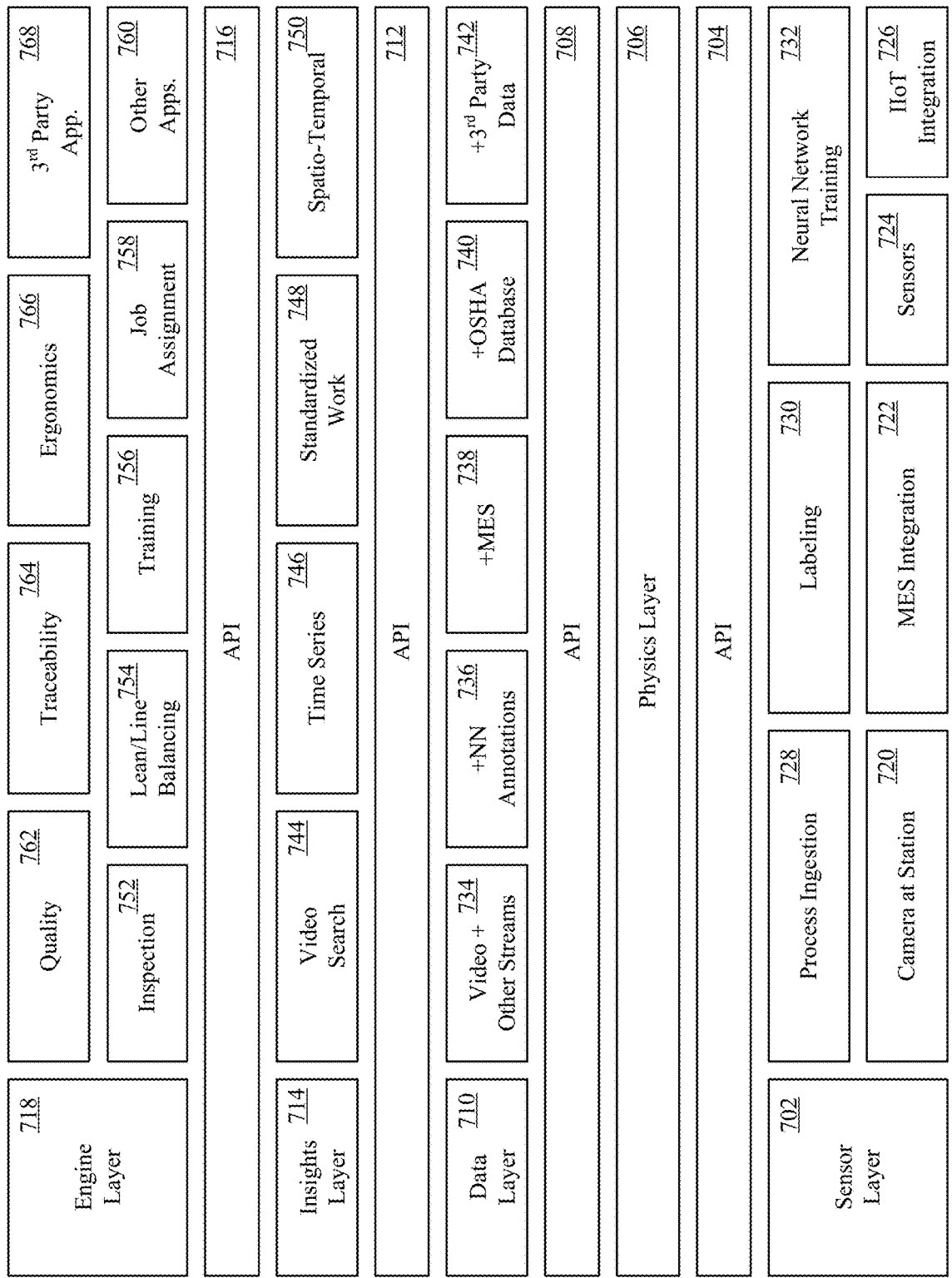
FIG. 7 shows an action recognition and analytics system, in accordance with aspects of the present technology.

Referring now to FIG. 7, an action recognition and analytics system, in accordance with aspects of the present technology, is shown. The action recognition and analytics system can include a plurality of sensor layers 702, a first Application Programming Interface (API) 704, a physics layer 706, a second API 708, a plurality of data 710, a third API 712, a plurality of insights 714, a fourth API 716 and a plurality of engine layers 718. The sensor layer 702 can include, for example, cameras at one or more stations 720, MES stations 722, sensors 724, IIoT integrations 726, process ingestion 728, labeling 730, neural network training 732 and or the like. The physics layer 706 captures data from the sensor layer 702 to passes it to the data layer 710. The data layer 710, can include but not limited to, video and other streams 734, +NN annotations 736, +MES 738, +OSHA database 740, and third-party data 742. The insights layer 714 can provide for video search 744, time series data 746, standardized work 748, and spatio-temporal 842. The engine layer 718 can be utilized for inspection 752, lean/line balancing 754, training 756, job assignment 758, other applications 760, quality 763, traceability 764, ergonomics 766, and third party applications 768.

Figure 8:
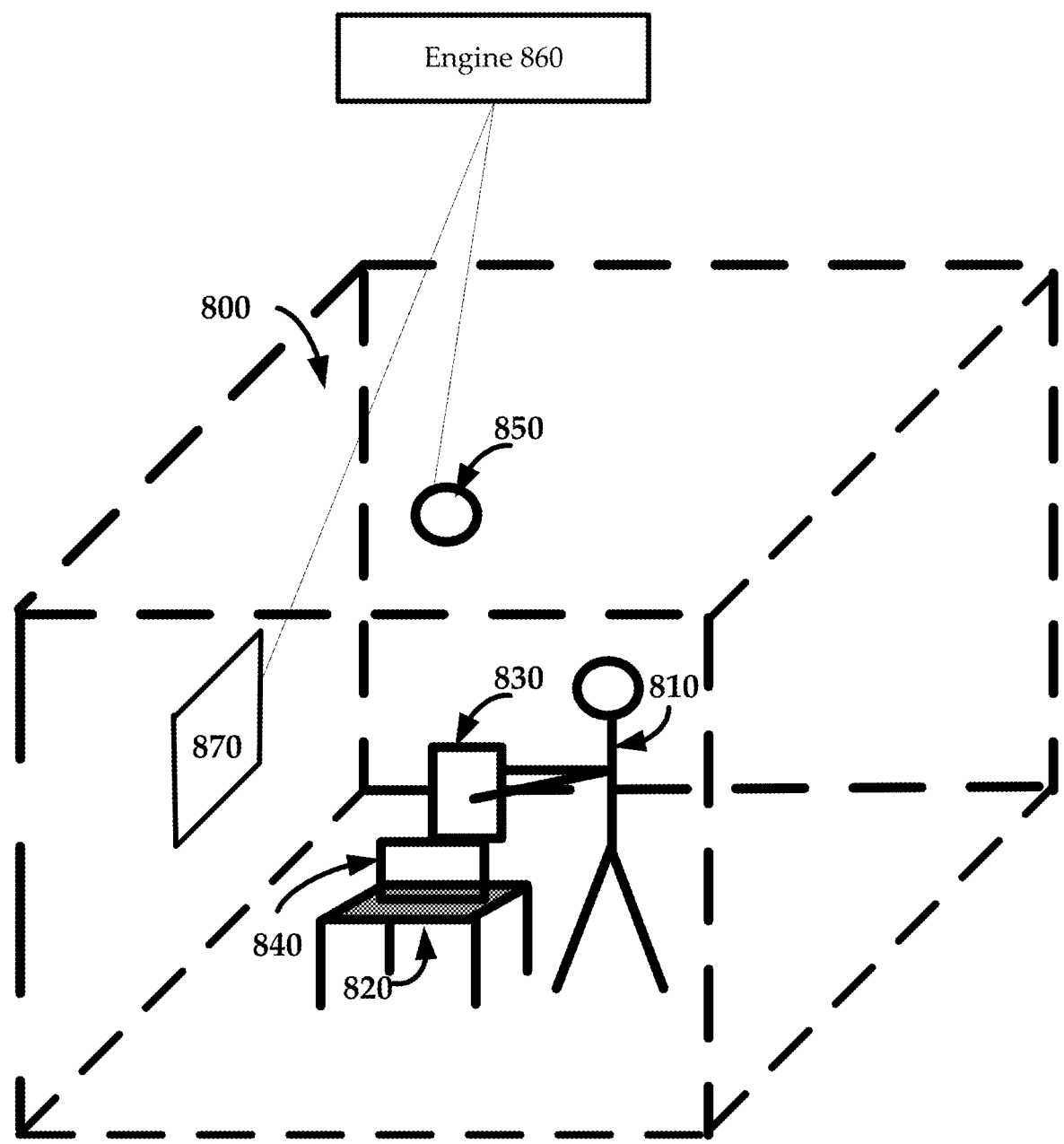
FIG. 8 shows an exemplary station, in accordance with aspects of the present technology

Referring now to FIG. 8, an exemplary station, in accordance with aspects of the present technology, is shown. The station 800 is an areas associated with one or more cycles, processes, actions, sequences, objects, parameters and or the like, herein also referred to as activity. Information regarding a station can be gathered and analyzed automatically. The information can also be gathered and analyzed in real time. In one exemplary implementation, an engine participates in the information gathering and analysis. The engine can use Artificial Intelligence to facilitate the information gathering and analysis. It is appreciated there can be many different types of stations with various associated entities and activities. Additional descriptions of stations, entities, activities, information gathering, and analytics are discussed in other sections of this detailed description.

A station or area associated with an activity can include various entities, some of which participate in the activity within the area. An entity can be considered an actor, an object, and so on. An actor can perform various actions on an object associated with an activity in the station. It is appreciated a station can be compatible with various types of actors (e.g., human, robot, machine, etc.). An object can be a target object that is the target of the action (e.g., thing being acted on, a product, a tool, etc.). It is appreciated that an object can be a target object that is the target of the action and there can be various types of target objects (e.g., component of a product or article of manufacture, an agricultural item, part of a thing or person being operated on, etc.). An object can be a supporting object that supports (e.g., assists, facilitates, aids, etc.) the activity. There can be various types of supporting objects, including load bearing components (e.g., a work bench, conveyor belt, assembly line, table top etc.), a tool (e.g., drill, screwdriver, lathe, press, etc.), a device that regulates environmental conditions (e.g., heating ventilating and air conditioning component, lighting component, fire control system, etc.), and so on. It is appreciated there can be many different types of stations with a various entities involved with a variety of activities. Additional descriptions of the station, entities, and activities are discussed in other sections of this detailed description.

The station 800 can include a human actor 810, supporting object 820, and target objects 830 and 840. In one embodiment, the human actor 810 is assembling a product that includes target objects 830, 840 while supporting object 820 is facilitating the activity. In one embodiment, target objects 830, 840 are portions of a manufactured product (e.g., a motherboard and a housing of an electronic component, a frame and a motor of a device, a first and a second structural member of an apparatus, legs and seat portion of a chair, etc.). In one embodiment, target objects 830, 840 are items being loaded in a transportation vehicle. In one embodiment, target objects 830, 840 are products being stocked in a retail establishment. Supporting object 820 is a load bearing component (e.g., a work bench, a table, etc.) that holds target object 840 (e.g., during the activity, after the activity, etc.). Sensor 850 senses information about the station (e.g., actors, objects, activities, actions, etc.) and forwards the information to one or more engines 860. Sensor 850 can be similar to sensor 135. Engine 860 can include a machine learning back end component, analytics, and front end similar to machine learning back end unit 180, analytics unit 190, and front end 190. Engine 860 performs analytics on the information and can forward feedback to feedback component 870 (e.g., a display, speaker, etc.) that conveys the feedback to human actor 810.

Figure 9:
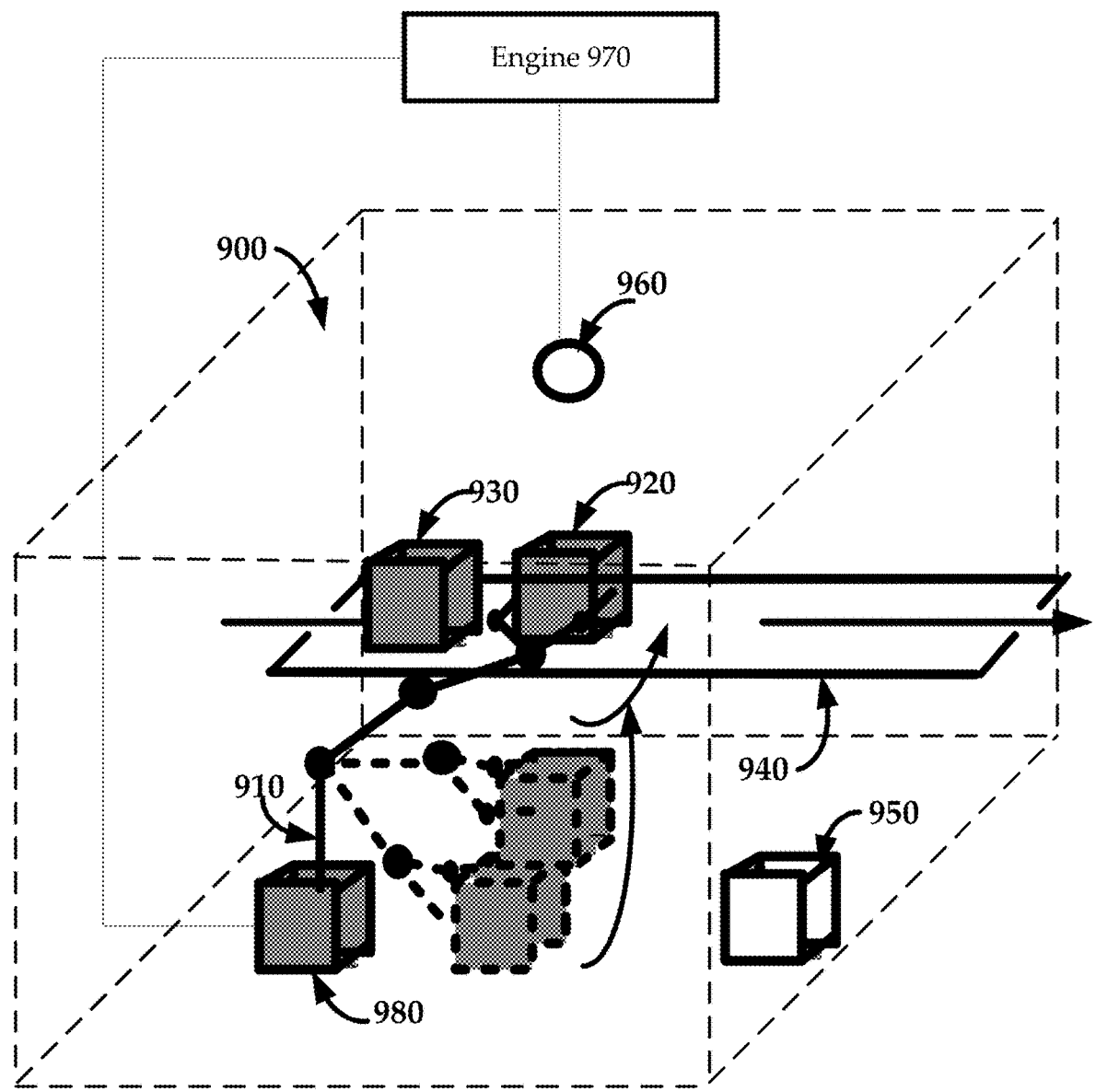
FIG. 9 shows an exemplary station, in accordance with aspects of the present technology

Referring now to FIG. 9, an exemplary station, in accordance with aspects of the present technology, is shown. The station 900 includes a robot actor 910, target objects 920, 930, and supporting objects 940, 950. In one embodiment, the robot actor 910 is assembling target objects 920, 930 and supporting objects 940, 950 are facilitating the activity. In one embodiment, target objects 920, 930 are portions of a manufactured product. Supporting object 940 (e.g., an assembly line, a conveyor belt, etc.) holds target objects 920, 930 during the activity and moves the combined target object 920, 930 to a subsequent station (not shown) after the activity. Supporting object 940 provides area support (e.g., lighting, fan temperature control, etc.). Sensor 960 senses information about the station (e.g., actors, objects, activities, actions, etc.) and forwards the information to engine 970. Engine 970 performs analytics on the information and forwards feedback to a controller 980 that controls robot 910. Engine 970 can be similar to engine 170 and sensor 960 can be similar to sensor 135.

A station can be associated with various environments. The station can be related to an economic sector. A first economic sector can include the retrieval and production of raw materials (e.g., raw food, fuel, minerals, etc.). A second economic sector can include the transformation of raw or intermediate materials into goods (e.g., manufacturing products, manufacturing steel into cars, manufacturing textiles into clothing, etc.). A third sector can include the supply and delivery of services and products (e.g., an intangible aspect in its own right, intangible aspect as a significant element of a tangible product, etc.) to various parties (e.g., consumers, businesses, governments, etc.). In one embodiment, the third sector can include sub sectors. One sub sector can include information and knowledge-based services. Another sub sector can include hospitality and human services. A station can be associated with a segment of an economy (e.g., manufacturing, retail, warehousing, agriculture, industrial, transportation, utility, financial, energy, healthcare, technology, etc,). It is appreciated there can be many different types of stations and corresponding entities and activities. Additional descriptions of the station, entities, and activities are discussed in other sections of this detailed description.

Figure 10:
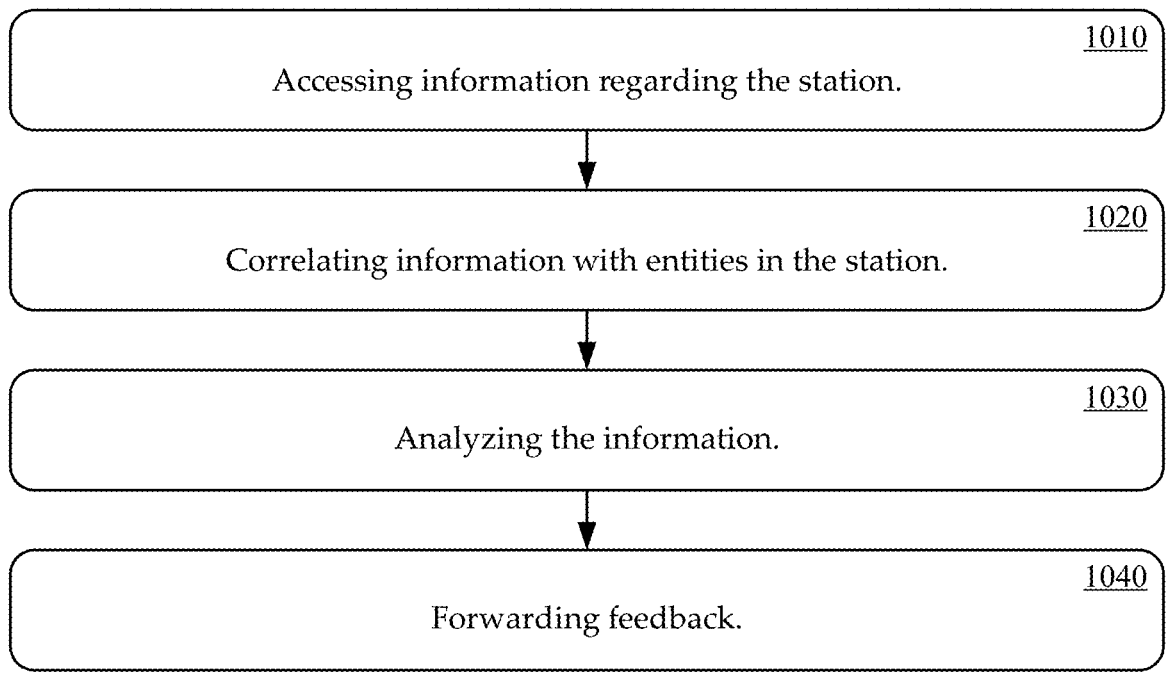
FIG. 10 shows an exemplary station activity analysis method, in accordance with one embodiment.

In one embodiment, station information is gathered and analyzed. In one exemplary implementation, an engine (e.g., an information processing engine, a system control engine, an Artificial Intelligence engine, etc.) can access information regarding the station (e.g., information on the entities, the activity, the action, etc.) and utilizes the information to perform various analytics associated with the station. In one embodiment, engine can include a machine learning back end unit, analytics unit, front end unit, and data storage unit similar to machine learning back end 180, analytics 185, front end 190 and data storage 175. In one embodiment, a station activity analysis process is performed. Referring now to FIG. 10, an exemplary station activity analysis method, in accordance with one embodiment, is shown.

At 1010, information regarding the station is accessed. In one embodiment, the information is accessed by an engine. The information can be accessed in real time. The information can be accessed from monitors/sensors associated with a station. The information can be accessed from an information storage repository. The information can include various types of information (e.g., video, thermal. optical, etc.). Additional descriptions of the accessing information are discussed in other sections of this detailed description At 1020, information is correlated with entities in the station and optionally with additional data sources. In one embodiment, the information the correlation is established at least in part by an engine. The engine can associate the accessed information with an entity in a station. An entity can include an actor, an object, and so on. Additional descriptions of the correlating information with entities are discussed in other sections of this detailed description.

At 1030, various analytics are performed utilizing the accessed information at 1010, and correlations at 1020. In one embodiment, an engine utilizes the information to perform various analytics associated with station. The analytics can be directed at various aspects of an activity (e.g., validation of actions, abnormality detection, training, assignment of actor to an action, tracking activity on an object, determining replacement actor, examining actions of actors with respect to an integrated activity, automatic creation of work charts, creating ergonomic data, identify product knitting components, etc.) Additional descriptions of the analytics are discussed in other sections of this detailed description.

At 1040, optionally, results of the analysis can be forwarded as feedback. The feedback can include directions to entities in the station. In one embodiment, the information accessing, analysis, and feedback are performed in real time. Additional descriptions of the station, engine, entities, activities, analytics and feedback are discussed in other sections of this detailed description, It is also appreciated that accessed information can include general information regarding the station (e.g., environmental information, generic identification of the station, activities expected in station, a golden rule for the station, etc.). Environmental information can include ambient aspects and characteristics of the station (e.g., temperature, lighting conditions, visibility, moisture, humidity, ambient aroma, wind, etc.).

It also appreciated that some of types of characteristics or features can apply to a particular portion of a station and also the general environment of a station. In one exemplary implementation, a portion of a station (e.g., work bench, floor area, etc.) can have a first particular visibility level and the ambient environment of the station can have a second particular visibility level. It is appreciated that some of types of characteristics or features can apply to a particular entity in a station and also the station environment. In one embodiment, an entity (e.g., a human, robot, target object, etc.) can have a first particular temperature range and the station environment can have a second particular temperature range.

The action recognition and analytics system 100, 500 can be utilized for process validation, anomaly detection and/or process quality assurance in real time. The action recognition and analytics system 100, 500 can also be utilized for real time contextual training. The action recognition and analytics system 100, 500 can be configured for assembling training libraries from video clips of processes to speed new product introductions or onboard new employees. The action recognition and analytics system 100, 500 can also be utilized for line balancing by identifying processes, sequences and/or actions to move among stations and implementing lean processes automatically. The action recognition and analytics system 100, 500 can also automatically create standardized work charts by statistical analysis of processes, sequences and actions. The action recognition and analytics system 100, 500 can also automatically create birth certificate videos for a specific unit. The action recognition and analytics system 100, 500 can also be utilized for automatically creating statistically accurate ergonomics data. The action recognition and analytics system 100, 500 can also be utilized to create programmatic job assignments based on skills, tasks, ergonomics and time. The action recognition and analytics system 100, 500 can also be utilized for automatically establishing traceability including for causal analysis. The action recognition and analytics system 100, 500 can also be utilized for kitting products, including real time verification of packing or unpacking by action and image recognition. The action recognition and analytics system 100, 500 can also be utilized to determine the best robot to replace a worker when ergonomic problems are identified. The action recognition and analytics system 100, 500 can also be utilized to design an integrated line of humans and cobot and/or robots. The action recognition and analytics system 100, 500 can also be utilized for automatically programming robots based on observing non-modeled objects in the work space.

There may be several steps or actions associated with a performance of an activity in a station. It is appreciated that some or portions of the actions can be performed by different/multiple actors. The capabilities of an actor can affect participation in an action. The capabilities can be rooted in the characteristics and features of the actors. Realization of objectives and proper performance of the activities often depends upon the various aspects of actors involved in performing the activity. There can be different actors (e.g., a human, a robot, a machine, etc.) which in turn can have various characteristics, attributes, features. For example, human actors can have instinct, reflex, intuition, and so on, but can also be prone to inconsistency, physical limitations, injury and other human frailties. A robot can have precision, controllable repeatability, untiring, hardy and so on, but lack intuition, intelligence, initiative, adaptability, and so forth. In addition to characteristics of the actors, realization of the objectives can be influenced by the work environment (e.g., manufacturing environments, service environments, medical environments, retail environments, etc.) and the nature of the activity itself (e.g., complex, simple, repetitive, non-uniform, hazardous, etc.).

The capabilities of multiple actors can be complementary and multiple actors participate in performance of an action/activity. In one embodiment, a robot performs a portion of task that correspond to robot advantages/strengths and a human performs a portion of a task that corresponds to human advantages/strengths. For example, the robot might move the heavy part and place it on a low friction turntable while the human might easily rotate the turntable and work on different sides of the heavy part. However, interaction of actors can have detrimental consequences. Conventionally, robots are frequently installed with protective fences to ensure that workers and robots do not work in overlapping spaces. Work in the 1990's by Akella et al lead to the development of cobots ("collaborative robots") that were designed to attempt to safely interact with human workers. However, conventional cobot approaches often have a number of issues (e.g., difficult to program, don't have an accurate information on the actual or real time conditions in a station, etc.). These issues can result in problematic and detrimental impacts (e.g., improper performance of an activity, incorrectly manufacturing a product, hazardous conditions, injury to actors, etc.). The most common conventional solution in the absence of accurate and complete worker motion data is to be overly conservative in the use/interaction of actors (e.g., cobots, humans, cobots, etc.) or in their location relative to other actors.

In one embodiment, interaction of actors in a station is examined. The examination can include monitoring activity and analyzing the activity. It is appreciated that various combinations of actors can be monitored and analyzed. For example, a human, robot, cobot or machine on its own, a human and a robot, a robot and a robot, a human and a plurality of other humans, a human and a plurality of robots, a robot and a plurality of other robots, and so on. It is appreciated the analysis results and corresponding feedback can facilitate realization of various objectives. The objectives can be associated with station configuration and activities. The station configuration can correspond to both configuration within a station and configuration of multiple stations. The station configuration can be based upon various factors (e.g., actor characteristics, type of activity, activity sequence etc.). The objectives can include station layout, activity assignment, dynamic activity allocation, and individual actor activity allocation.

FIG. 11 is a flow chart of an actor coordination method 1100 in accordance with one embodiment. In block 1110, respective information associated with a first actor and a second actor is accessed. The information can include sensed activity information. The information can be accessed in real time, on-demand, post-facto, and so on. The sensed activity information can be associated with a grid within the activity space. There can be various combinations of actors (e.g., human and device, human and human, device and device, etc.)

In block 1120, the information is analyzed, including analyzing activity of the first actor with respect to a second actor. The information can be analyzed in real time, on-demand, post-facto, and so on. The analyzing can include automated artificial intelligence analysis.

In block 1130, respective feedback is forwarded based on the results. The feedback can include an indication of a change to the first actor, second actor, or both. The feedback can include a collective objective with respect to the first actor or the second actor. The objectives can include station layout, activity assignment, dynamic activity allocation, and individual actor activity allocation. The feedback can be forwarded in real time, on-demand, post-facto, and so on.

In one embodiment, the analysis and feedback are directed to station configuration. In one exemplary implementation, the feedback is used to determine (e.g., design, move, etc.) the location of the station, an entity, an activity, and so on. In one exemplary implementation, the feedback is configured to facilitate design/build/remodel of a station. In one exemplary implementation, the feedback is configured to facilitate assignment of an activity to a station. In one embodiment, the feedback includes an indication of which activity is assigned to which station. The station can be included in an assembly line. The analysis and feedback can be based on various combinations/permutations of entities. A combination of various types of actors (e.g., human, programmable device, robot, cobot, hard device, etc.) can be implemented.

In one embodiment, the analysis and feedback are directed to activity assignment. In one embodiment, an engine identifies which activities to assign to which type of actor. In one exemplary implementation, an engine senses/measures characteristics/features/capabilities of a plurality of actors performing an activity. The plurality of actors can include different types of actors.

In one embodiment, the analysis and feedback are directed to dynamic activity allocation. When the stations are configured and the activity assignment implemented, results can can be updated dynamically as an engine senses/monitors corresponding activities and actors (e.g., skills, capabilities, features, etc.). Dynamic activity allocation can be utilized to check if the station configuration and activity assignment are actually reaching and maintaining objectives.

In one embodiment, the analysis and feedback are directed to individual actor activity allocation. An engine can access and analyze information on an individual actor basis or a group/plurality of actors basis. In one embodiment, the access and analysis can be performed in real time. In one exemplary implementation, the engine can optimize activity performance both individually and collectively. In one embodiment, feedback can include assignment of an activity to a station.

In one embodiment, engine feedback can help realization of significant flexibility compared to traditional systems.

In one embodiment, an engine system can observe actors executing activities. In one exemplary implementation, observing and analyzing robots is easier than humans, since the variability in the robot motion is much lower. Having observed the actors (e.g., both humans and robots working, cobots working, multiple humans, etc.) the engine can provide recommendations to optimally ensure safe and productive activities. In one embodiment, ergonomic hazards (e.g., cumulative musculoskeletal disorders) for a human can be identified and an appropriate replacement robot or cobot can be utilized (e.g., based upon a corresponding time and motion study, identified from a library of available robots, etc.). In one embodiment, human and robot data can be used to identify tasks that might be better served by another actor because of challenges the actor might be facing. Actor coordination analysis can help minimize the footprint based on motions of the actors working together. In one embodiment, the same design process is run on a human-machine system.

An engine can observe the actors (e.g., human and machine, cobot and robot, etc.) performing activities. The engine can determine the work envelopes and time and motion studies of the actors, and can substitute representative and probabilistic models for simulation purposes. In one embodiment, the engine identifies co-activity spaces by overlaying reach, motion and action data. The engine can use mathematical techniques from simply overlaying spatial work envelopes to spatio-temporal representations to determine the relative positions of entities (e.g., an assembly line, a worker, a product component, a robot/cobot system, a machine, etc.). The engine can also determine kinematic and dynamic properties of actions associated with the entities. In one exemplary implementation, safety is the primary cost function and the information is used to identify safer parts of actor work envelopes avoid safety issues.

FIG. 12 is a flow cart of another actor interaction 1200 in accordance with one embodiment.

In block 1210, information associated with a first actor and second actor is accessed. The information can include sensed activity information within an activity space with respect to performing an activity.

In block 1220, the activity information is analyzed, including analyzing activity of the first actor and analyzing activity of the second actor. The analyzing includes determination of a work envelope and time/motion study for both the first actor and the second actor. The analyzing can include identification of co-working spaces by overlaying spatial work/task envelope information. The work/task envelope can include reach, motion, and action data. The analyzing can be based on representative and probabilistic models for simulation purposes. The analyzing can include utilization of spatio-temporal representations to determine the relative position of the assembly line, the first actor, and the second actor. The analyzing includes determination of kinematic and dynamic properties of the assembly line, the first actor, and the second actor. The analyzing includes determination of safer parts of a work envelope.

In block 1220, the activity information is analyzed, including analyzing activity of the first actor and analyzing activity of the second actor. The analyzing includes determination of a work envelope and time/motion study for both the first actor and the second actor. The analyzing can include identification of co-working spaces by overlaying spatial work/task envelope information. The work/task envelope can include reach, motion, and action data. The analyzing can be based on representative and probabilistic models for simulation purposes. The analyzing can include utilization of spatio-temporal representations to determine the relative position of the assembly line, the first actor, and the second actor. The analyzing includes determination of kinematic and dynamic properties of the assembly line, the first actor, and the second actor. The analyzing includes determination of safer parts of a work envelope.

In block 1230, respective feedback is forwarded. The feedback is based on the results of the analysis from block 1220.

Figure 13:
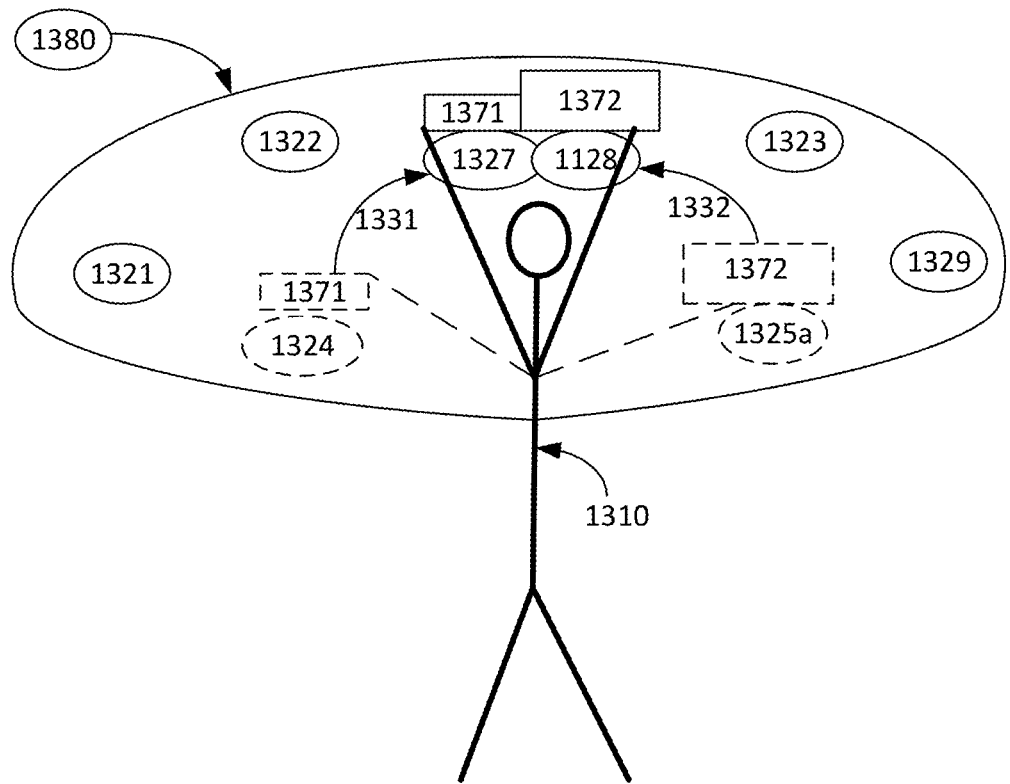
FIG. 13 is a block diagram of an exemplary human actor in a station in accordance with one embodiment.

FIG. 13 is a block diagram of human actor 1310 in a station 1300 in accordance with one embodiment. Station 1300 includes human actor 1310 with access to reach points 1321, 1322, 1323, 1324, 1325, 1326, 1327, 1328, and 1329. The human actor 1310 is shown coupling two product components by moving a first product component 1371 at reach point 1324 to reach point 1327 via motion 1331 and a second component 1372 at reach point 1325 to reach point 1328 via motion 1332.

In one embodiment, an engine accesses and analyzes information on station 1300 and the activity of human actor 1300 coupling the two product components 1371 and 1372. The engine builds one or more data structures with information regarding an activity space associated with the activity. The activity space information in the one or more data structures can come from various sources. A portion of the activity space information can be generated by the engine based upon sensed/monitored information from the station (e.g., information associated with: human actor 1310, product components 1371 and 1372, etc.). A portion of the activity space information can be accessed from other sources (e.g., third parties, product specifications, OSHA, etc.). The engine can use the information to create/generate additional information associated with the station, and entity, activity or so on (e.g., a virtual representation of the work activity space, a work space envelope. etc.). In one embodiment, the engine generates/creates a data structure and virtual representation of work envelope 1380. In one exemplary implementation, the engine can generate/create a data structure with additional information (e.g., forces/velocities applied to product components 1371 and 1372, torque at various points on human actor 1310, etc.).

In one embodiment, a detailed activity space representation for a number of actors and activities is created. The activity space can be multi-dimensional (e.g., 3D, 6D, etc.). Creating a virtual activityspace and comparing actors and activities to the virtual activity space can save on costs of setting up an actual work space. The virtual activity space can include grid points corresponding to grid locations in a real world work space. The virtual activity space can include information regarding an activity, constraints, and various metrics, including reach, payload, reliability, speed, physical space available for a second actor to be installed. Next, engine analytics copares or overlays this n dimensional activity space with those of a number of candidateactors. It then scores the overlap of the activityspaces using different measurements (e.g., reach, speed, dynamics, payload etc). The engine can use the scores to facilitate selection/identification of a replacement robot.

An engine can use the activity space information to facilitate selection of a replacement actor a human.

Figure 14:
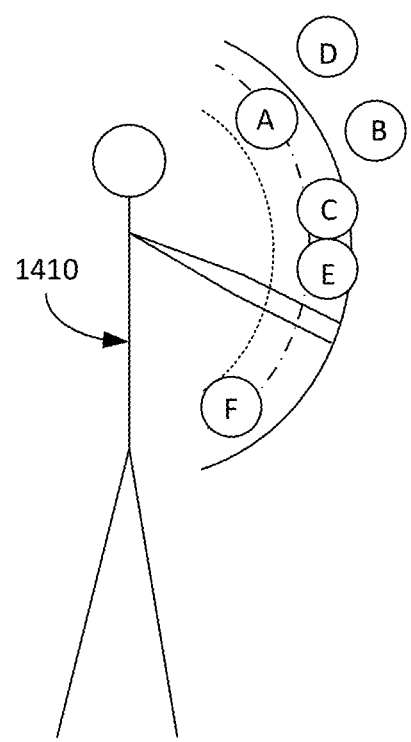
FIG. 14 is a side view of an exemplary reach scenario in a station is shown in accordance with one embodiment.

Referring now to FIG. 14, a side view of an exemplary reach scenario in a station is shown in accordance with one embodiment. The reach scenario shows six reach locations A through F. The locations can correspond to a zone (e.g., a primary reach zone, a secondary reach zone, a tertiary reach zone, etc.). The reach locations can be associated with activities (e.g., motions, tasks, actions, etc.) performed by actor 1410.

In one embodiment, an engine performs an analysis of the reach scenario and corresponding activities. The analysis can include identification of the reach points (e.g., based on sensed/monitored information from the station, third party information, etc.). In one embodiment, the engine generates a data structure based on the analysis of an activity in a station. The data structure can include information associated with a reach scenario. The table below is a block diagram of an exemplary data structure in accordance with one embodiment of the present invention. In one exemplary implementation, the table corresponds to the reach scenario in FIG. 14.

TABLE 5

| | Location | | | | | |
|---|---|---|---|---|---|---|
| | A | B | C | D | E | F |
| Reach Distance (Millimeter) | 455 | 955 | 357 | 1165 | 357 | 245 |
| Frequency | 321 | 311 | 311 | 331 | 421 | 321 |
| Payload Weight (Grams) | 2 | 2 | 3 | 2 | 2.5 | 4 |
| Torque (Norton Millimeters) | 8.92 | 18.73 | 10.50 | 22.85 | 8.75 | 9.61 |

The location row includes identification of the locations of the reach point. The reach distance row includes distances of the reach point from the actor. The frequency is the number of time the actor motions to the reach point location. The payload weight is the weight of an object the actor is supporting/holding at the reach point. It is appreciated that payload weights can change as components are added/removed due to an activity at a reach point. In one embodiment, the heaviest weight of the object (e.g., before component is removed, after a component is added, etc.) at a reach point is used to calculate torque at a reach point. An engine can access a sensed measurement of a torque, a calculated torque (e.g., based on the distance of an object from a moment/twist point and weight of an object, etc.).

Figure 15:
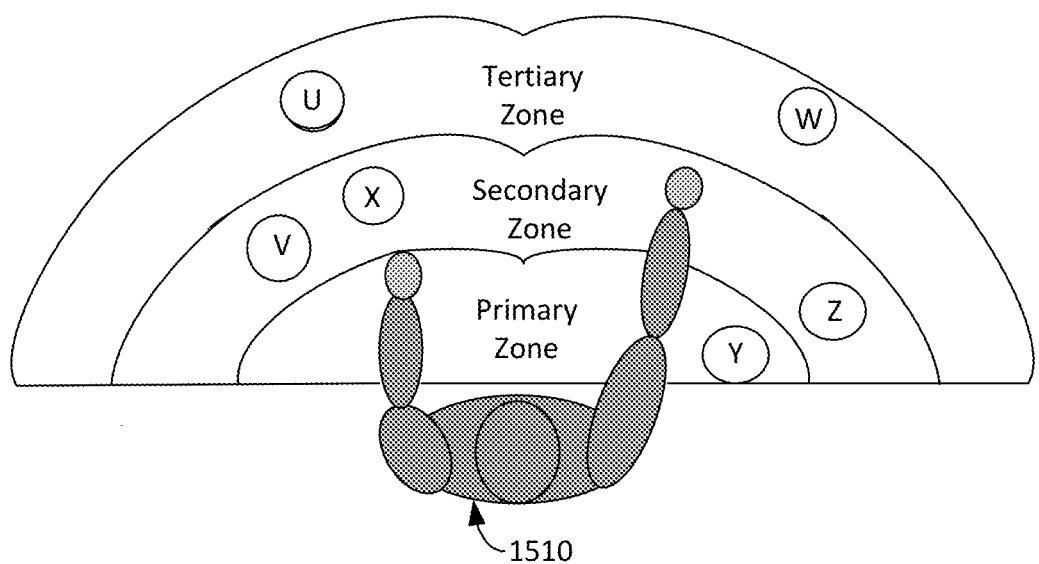
FIG. 15 is a top down view of another exemplary reach scenario in a station is shown in accordance with one embodiment.

Referring now to FIG. 15 is a top down view of another exemplary reach scenario in a station is shown in accordance with one embodiment. The reach scenario shows six reach locations U through Z. The locations can correspond to a zone (e.g., a primary reach zone, a secondary reach zone, a tertiary reach zone, etc.). The reach locations can be associated with activities (e.g., motions, tasks, actions, etc.) performed by actor 1510.

In one embodiment, an engine performs an analysis of the reach scenario and corresponding activities. The analysis can include identification of the reach points (e.g., based on sensed/monitored information from the station, third party information, etc.). The engine analysis can also include identification of zones (e.g., a primary zone, a secondary, zone, a tertiary zone, etc.) in which a respective one or more of the reach points are located. The zones can correspond to different characteristics (e.g., distance from an actor, load constraints, etc.). In one embodiment, a primary zone and tertiary zone (e.g., respectively close and far distances from the actor) correspond to locations that are relatively awkward to reach (e.g., need to lean back, need to lean forward, pick up parts from a particular orientation, etc.). In one exemplary implementation, a load limit in a secondary zone can be higher than a tertiary zone (e.g., the tertiary zone can put higher torque strain on an actor's supporting member/component, arm, joint, pivot point, etc.).

In one embodiment, the engine generates a data structure based on the analysis of an activity in a station. The data structure can include information attached kinematics (e.g., attributes, motion, reach, velocity, etc.) and matched dynamics (e.g., torque, force, etc.) associated with a reach scenario. In one embodiment, the data structure can include spatio-temporal information related to activities of an actor in the work space. FIG. 16 is a block diagram of an exemplary data structure in accordance with one embodiment. The activity and corresponding starting coordinates and ending coordinates can be An engine can produce motion data from worker's hands starting position (e.g., x, y, z, roll, pitch and yaw) to ending position (e.g., x1, y1, z1, roll1, pitch1, yaw1). The motion data can include the movement distance $P(x,y,z)$ minus $P(x1, y1, z1)$. It can also be computed in six dimensional space. This data can be analyzed over a time-period for repetitive motions to identify ergonomic issues developing across long periods. This is shown by the dates and times, identified actions, starting coordinates, and in coordinates, the weight of the item, and the movement distance. In one embodiment, a correlation to between the activity and a reach point is established. The activities can be similar to those in the data structure of FIG. 16 and the reach points can be similar to the reach scenario data structure above). In one exemplary implementation, identifying coordinates corresponding to reach points (e., reach points A through F, U through Z, etc.) can be created by the engine using the information in the table shown above an in FIG. 16.

It is appreciated the actor coordination can be associated with various objectives. In one embodiment, the objectives are associated with various cost functions. A cost function can include throughput of the system. If an actor is adversely impacting throughput, the corresponding activity can be assigned (e.g., re-assigned, transferred, moved, etc.) to another actor. In one exemplary implementation, when an actor is having difficulty with a particular activity or action the activity or action can be re-assigned to another actor. The other actor can be the same station or a different station. In one embodiment, a cost function is associated with system quality. If an actor is impact the quality of the system (e.g., product defects, service mistakes, etc.) the activity can be reassigned to another actor. In one embodiment, a cost function is associated with the configuration or layout of a station or group of stations. The stations can be included in an assembly line.

Various things can impact configuration and layout. In one embodiment, it is prudent to provide a significant amount of space between actors. The space can help prevent detrimental impacts and accidents between actors. Providing significant amount of space can require a lot of room or real estate. Configuration and layout can be impacted by precautionary measures with respect to actors' activities. In one embodiment, an actor can be located in a protective enclosure (e.g., cage, etc.) which can increase the area or "footprint" occupied by an actor. In one embodiment, precautionary characteristics and features can be included for an actor without increasing the area or footprint. In one exemplary implementation, a cobot has characteristics and features that make it relatively safer to work in closer proximity to a human than a robot.

Figure 17:
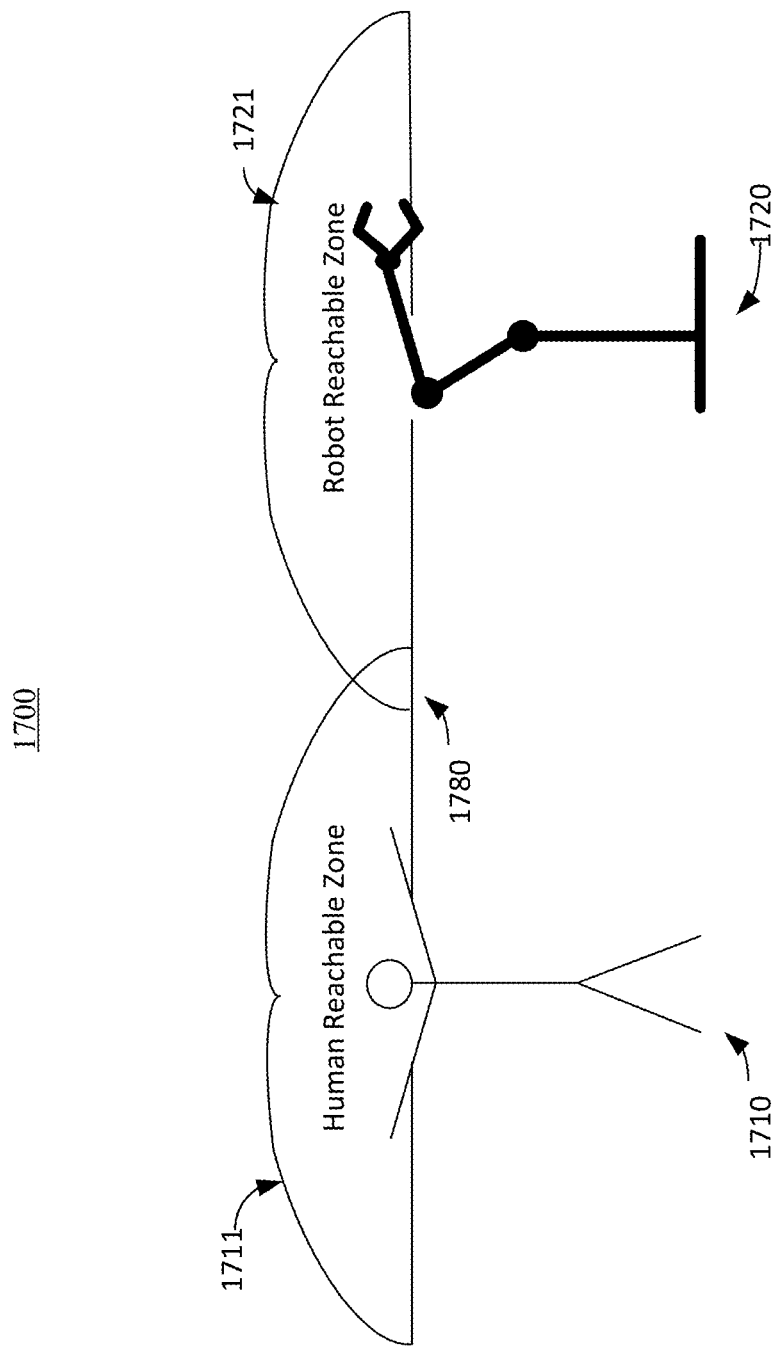
FIG. 17 is a block diagram of an exemplary co-work space of a human actor and a robot actor in accordance with one embodiment.

FIG. 17 is a block diagram of a co-work space 1700 of a human actor and a robot actor in accordance with one embodiment. Co-work space 1700 includes human actor 1710 with a human reachable activity space 1711 and robot actor 1720 with a reachable activity space 1721. The overlap area 1780 is collaborative space between human and robot. In one embodiment, activity space modeling and analysis (e.g., performed by engine 170, etc.) determines this collaborative space is a potential problem (e.g., robot poses safety issue for a human actor, the collaboration tends to cause problems, etc.). The engine can suggest feedback solutions. In one embodiment, an engine accesses information (e.g., regarding reach limits, safety activity spaces, sequence of tasks, etc.), and can provide various recommendations (e.g., change an actor location, change type of actor etc.).

Figure 18:
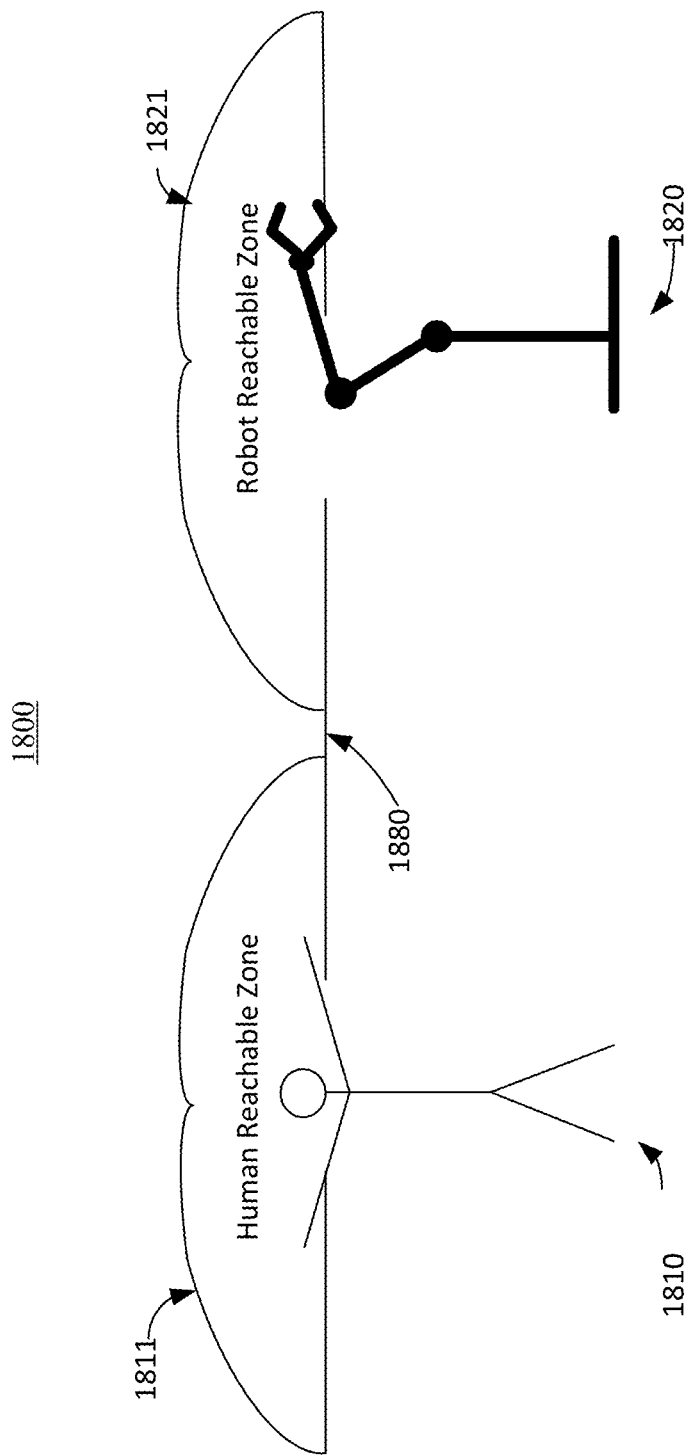
FIG. 18 is a block diagram of an exemplary co-work space in accordance with one embodiment.

FIG. 18 is a block diagram of a co-work space 1800 in accordance with one embodiment. Co-work space 1800 includes a first actor 1810 with a first reachable activity space 1811 and a second actor 1820 with a second reachable activity space 1821. In one embodiment, first actor 1910 is a human actor and second actor 1920 is a robot actor. An engine can suggest a re-configuration of an actor layouts/position. In one embodiment, the engine suggests locating the first actor 1810 and the second actor 1820 so that there is a space 1880 between the respective activity spaces.

Figure 19:
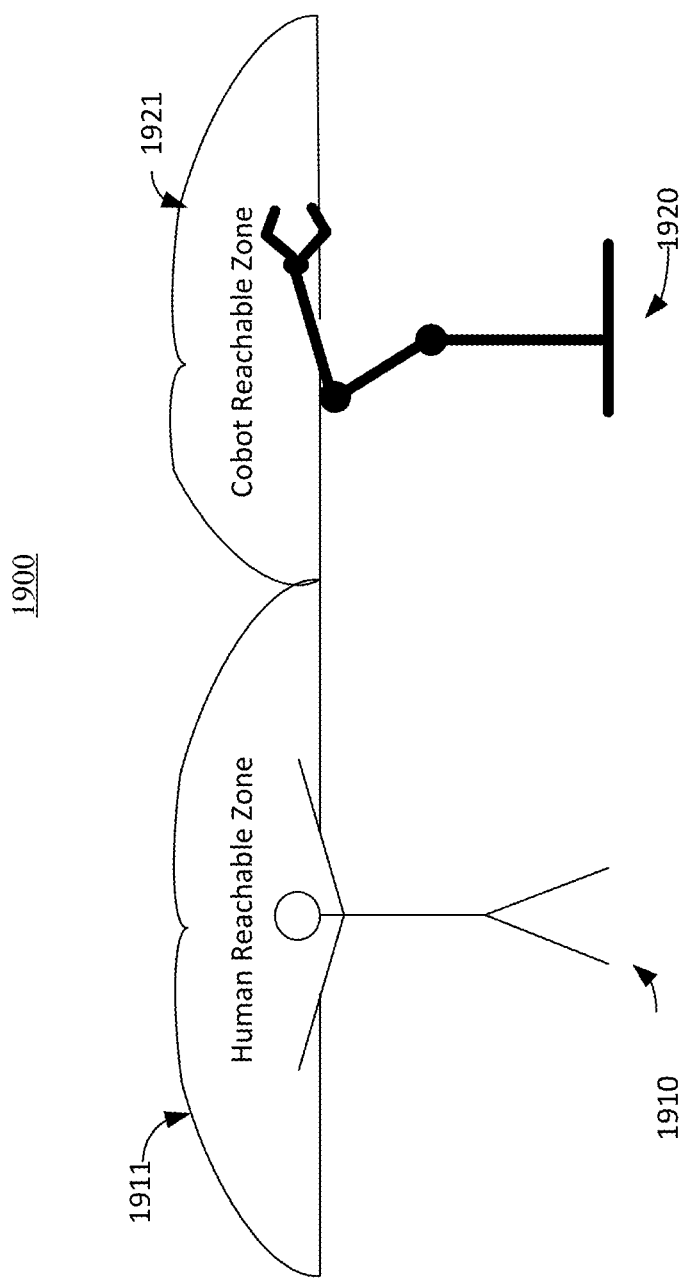
FIG. 19 is a block diagram of an exemplary co-work space in accordance with one embodiment.

FIG. 19 is a block diagram of a co-work space 1900 in accordance with one embodiment. Co-work space 1900 includes first actor 1910 with a first reachable activity space 1911 and second actor 1920 with a second reachable activity space 1921. In one embodiment, first actor 1910 is a human actor and second actor 1920 is a cobot actor. An engine can suggest a re-allocation of an activity to a cobot. In one embodiment, the engine suggests a cobot that is programmed not to infringe on the human reachable activity space. In one embodiment, a cobot is programmed to efficiently and safely operate in the human reachable activity space.

Figure 20:
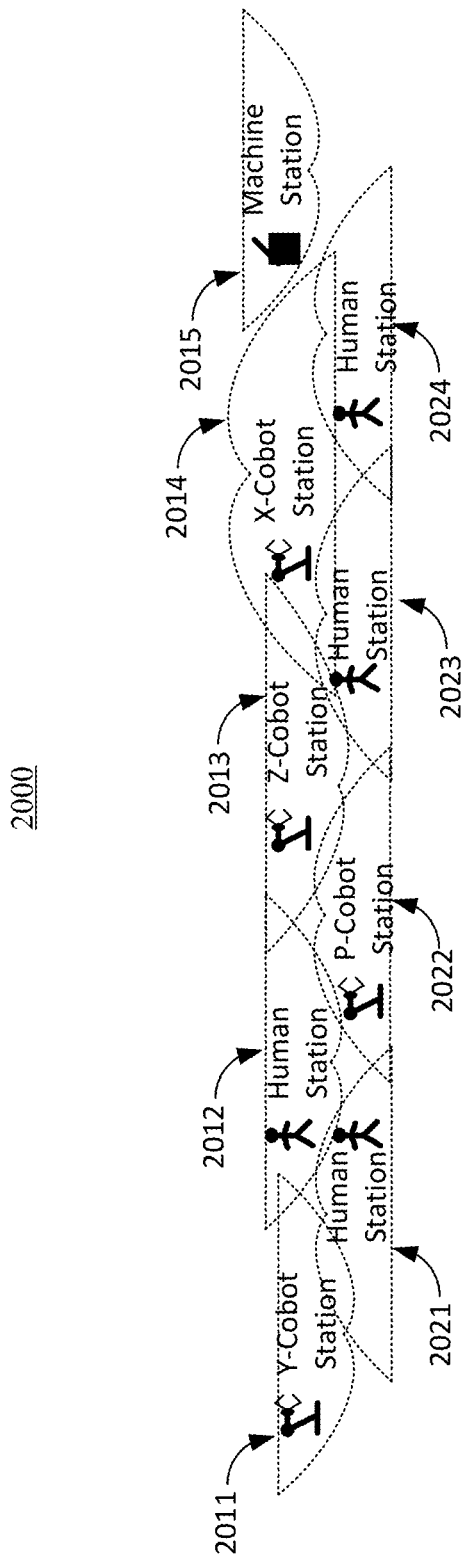
FIG. 20 is a block diagram of an exemplary co-work space layout configuration in accordance with one embodiment.

FIG. 20 is a block diagram of co-work space layout configuration 2000 in accordance with one embodiment. Co-work space layout configuration 2000 includes human actors in activity spaces 2021, 2012, 2023 and 2024, cobot actors in activity spaces 2011, 2022, 2013, and 2014, and a machine activity station 2015. In one embodiment, co-work space layout configuration 2000 is included in an assembly line. In one embodiment, the cobots are programmed to cross over and operate in human activity spaces and allow humans to crossover and operate in cobot activity spaces. An engine can recommend efficient assembly line/factory layouts based upon activity space analysis of the respective actors.

Figure 21:
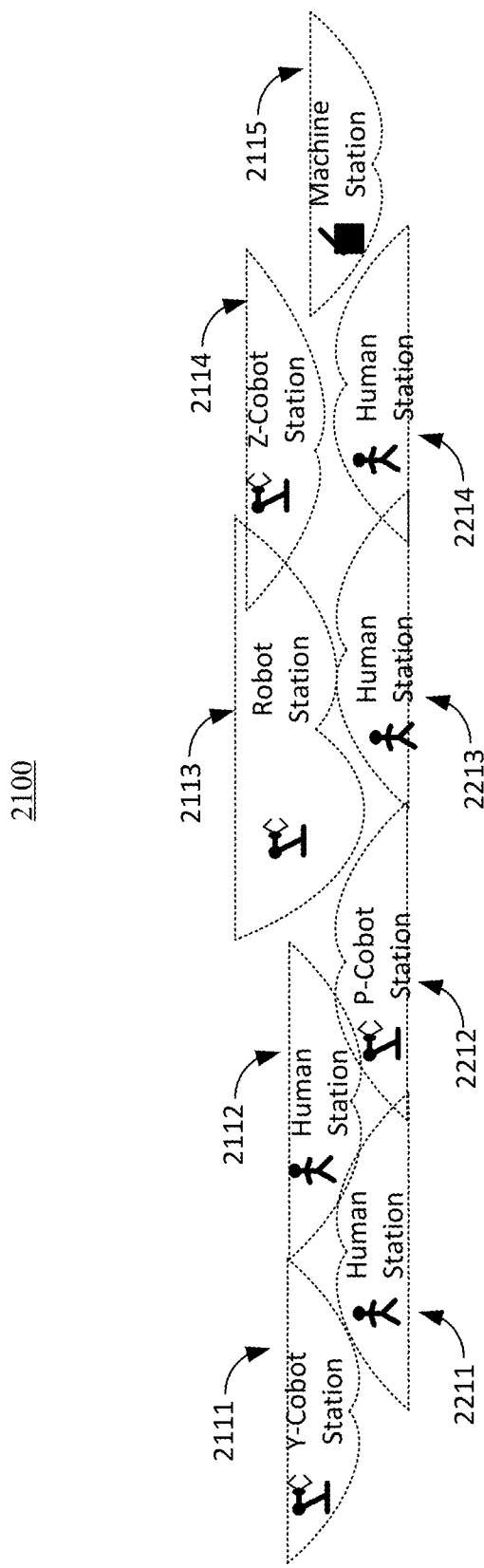
FIG. 21 is a block diagram of an exemplary co-work space layout configuration in accordance with one embodiment.

FIG. 21 is a block diagram of co-work space layout configuration 2100 in accordance with one embodiment. In one embodiment, co-work space layout configuration 2100 is included in an assembly line. Co-work space layout configuration 2000 includes human actors in activity spaces 2211, 2112, 2213 and 2214, cobot actors in activity spaces 2111, 2212, and 2114, and robot station 2113 and a machine activity station 2115. In one embodiment, co-work space layout configuration 2100 is configured so that robot station 2213 can not cross over into a human activity space but can cross over into cobot activity space 2114. Ione embodiment, the cobots are programmed to cross over and operate in human activity spaces and robot activity spaces, and also allow humans and robots to crossover and operate in cobot activity spaces. An engine can recommend efficient assembly line/factory layouts based upon activity space analysis of the respective actors.

In one embodiment, the actor coordination and assignment to activities is based on activity key performance indicators (KPIs) like throughput, quality, one can layout, a line with a minimal foot print. A key performance indictor (KPI) is a measurable value that demonstrates how effectively a company is achieving key business decisions. A KPI can be used to evaluate success at reaching targets. KPIs evaluate the success of an organization or of a particular activity (such as projects, programs, products, and other initiatives, etc.).

The analysis can include an indication of a condition/situation. The condition/situation can be associated with various aspects of an entity and corresponding activity (e.g., a component, a part, a process step, etc.). The condition/situation can be an existing condition that has been specifically sensed/detected. The analysis and corresponding condition/situation can have a predictive aspect/nature (e.g., impending condition, future state, anticipated action, etc.). The respective feedback can include a directive/control for the first actor, for the second actor, or for both. The respective feedback can be a directive/control to change the respective one of the first actor or second actor to avoid a collision (detrimental contact with each other).

In one exemplary implementation, a condition/situation corresponds to proper performance of an action (e.g., without defect, safely, etc.). A condition/situation can be associated with a detrimental scenario (e.g., a hazardous condition, a collision, overheating, a missed/skipped action, a task performed incorrectly, a defective element, wrong component used, a part not properly installed, etc.). In one embodiment, a prediction regarding movement can be made to determine if a dangerous circumstance/collision is going to happen before a harmful impact occurs. Feedback based on the analysis can be provided. The feedback can enable avoidance of detrimental conditions/situations.

FIG. 22 is a flow cart of another actor interaction method 2200 in accordance with one embodiment.

In block 2210, accessing in real time respective information associated with a first actor and a second actor, including sensed activity information. The accessing can includes continually sensing activity associated with the first actor and a second actor. The analyzing includes determining respective work envelopes associated with the first actor and a second actor.

In block 2220, analyzing the information in real time, including analyzing activity of the first actor with respect to a second actor.

An engine can observe the actors (e.g., human and machine, cobot and robot, etc.) at work. The engine can determine the work envelopes and time and motion studies of the actors, substituting representative and probabilistic models for them when required for simulation purposes. In one embodiment, the engine identifies co-working spaces by overlaying reach, motion and action data. The engine can use mathematical techniques from simply overlaying spatial work envelopes to spatio-temporal representations to determine the relative positions of entities (e.g., an assembly line, a worker, a product component, a robot/cobot system, etc.). The engine can also determine kinematic and dynamic properties of actions associated with the entities. In one exemplary implementation, safety is the primary cost function and the information is used to identify safer parts of actor work envelopes avoid safety issues.

In block 2230, forwarding respective feedback based on the results of the analysis to the first actor and the second actor when the results include an indication of a change to the first actor or second actor. The feedback can be forwarded in real time. In one embodiment, the feedback includes a direction/command to change activity of the first actor or second actor and is based on a prediction. The prediction can include an indication of a detrimental activity by the first actor or second actor. The detrimental activity can be one predicted to result in an undesirable collision between the first actor and second actor. In one embodiment, the analyzing and feedback are provided in sufficient time to permit a change that avoids the detrimental activity. The feedback can include a direction to stop/pause an event activity (e.g., stop a robot/human from doing a step wrong, causing damage, etc.). The feedback can include a corrective aspect (e.g., insert a previously missed part, an order/command for actor to stop/take evasive measure, etc.).

The corrective action can be directed to a co-actor. In one embodiment, the corrective action can be an order to a first actor to engage in an action/activity to correct an action by another actor. A first actor may be performing a task incorrectly and a second actor may be directed to stop/correct the action from causing damage. In one exemplary implementation, a robot is directed to correct an activity performed by a human or another robot (e.g., the robot inserts a part missed by a robot, a human correct a step performed by a robot, etc.). In one exemplary implementation, a human is directed to correct an activity performed by a robot or another human (e.g., the human inserts a part missed by a robot, a human correct a step performed by a robot, etc.). In one embodiment, the corrective action can be an order to a first actor to engage in an action/activity to protect another actor.

In one embodiment, an engine system can observe actors executing tasks. In one exemplary implementation observing robots is much easier, since the variability in their motion is much lower. Having observed the actors (e.g., both humans and robots working, cobots working, multiple humans, etc.) the engine can provide recommendations to optimally ensure safe and productive activities. In one embodiment, ergonomic hazards for a human can be identified and an appropriate replacement robot or cobot can be utilized (e.g., based upon a corresponding time and motion study, identified from a library of available robots, etc.). In one embodiment, human and robot data can be used to identify tasks that might be better served by another actor because of challenges the actor might be facing. For humans and robots data, a deep learning system can help minimize the footprint based on motions of robots and humans working together. In other words, run the same design process on a human-machine system.

Figure 23:
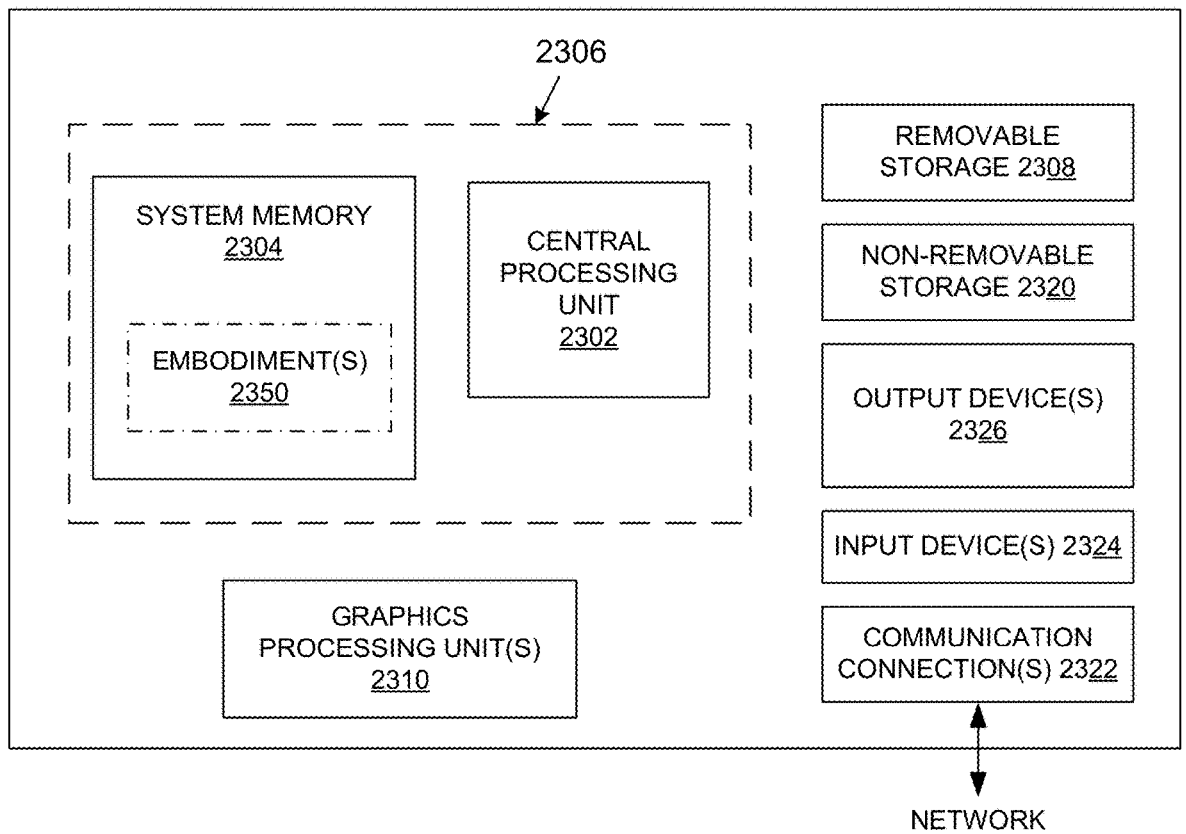
FIG. 23 shows a block diagram of an exemplary computing system upon which one or more various embodiments described herein may be implemented in accordance with one embodiment.

FIG. 23 shows a block diagram of an example of a computing system 2300 upon which one or more various embodiments described herein may be implemented in accordance with various embodiments of the present disclosure. In various embodiments, the computer system 2300 may include a cloud-based computer system, a local computer system, or a hybrid computer system that includes both local and remote devices. In a basic configuration, the system 2300 includes at least one processing unit 2302 and memory 2304. This basic configuration is illustrated in FIG. 23 by dashed line 2306. The system 2300 may also have additional features and/or functionality. For example, the system 2300 may include one or more Graphics Processing Units (GPUs) 2310. Additionally, the system 2300 may also include additional storage (e.g., removable and/or non-removable) including, but not limited to, magnetic or optical disks or tape. Such additional storage is illustrated in FIG. 23 by removable storage 2308 and non-removable storage 2320.

The system 2300 may also contain communications connection(s) 2322 that allow the device to communicate with other devices, e.g., in a networked environment using logical connections to one or more remote computers.

Furthermore, the system 2300 may also include input device(s) 2324 such as, but not limited to, a voice input device, touch input device, keyboard, mouse, pen, touch input display device, etc. In addition, the system 2300 may also include output device(s) 2326 such as, but not limited to, a display device, speakers, printer, etc.

In the example of FIG. 23, the memory 2304 includes computer-readable instructions, data structures, program modules, and the like associated with one or more various embodiments 2350 in accordance with the present disclosure. However, the embodiment(s) 2350 may instead reside in any one of the computer storage media used by the system 2300, or may be distributed over some combination of the computer storage media, or may be distributed over some combination of networked computers, but is not limited to such.

It is noted that the computing system 2300 may not include all of the elements illustrated by FIG. 23. Moreover, the computing system 2300 can be implemented to include one or more elements not illustrated by FIG. 23. It is pointed out that the computing system 2300 can be utilized or implemented in any manner similar to that described and/or shown by the present disclosure, but is not limited to such.

Some portions of the detailed descriptions are presented in terms of procedures, logic blocks, processing, and other symbolic representations of operations on data bits within a computer memory. These descriptions and representations are the means generally used by those skilled in data processing arts to effectively convey the substance of their work to others skilled in the art. A procedure, logic block, process, etc., is here, and generally, conceived to be a self-consistent sequence of steps or instructions leading to a desired result. The steps include physical manipulations of physical quantities. Usually, though not necessarily, these quantities take the form of electrical, magnetic, optical, or quantum signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are associated with the appropriate physical quantities and are merely convenient labels applied to these quantities. Unless specifically stated otherwise as apparent from the following discussions, it is appreciated that throughout the present application, discussions utilizing terms such as "processing", "computing", "calculating", "determining", "displaying" or the like, refer to the action and processes of a computer system, or similar processing device (e.g., an electrical, optical or quantum computing device) that manipulates and transforms data represented as physical (e.g., electronic) quantities. The terms refer to actions and processes of the processing devices that manipulate or transform physical quantities within a computer system's component (e.g., registers, memories, other such information storage, transmission or display devices, etc.) into other data similarly represented as physical quantities within other components.

The foregoing descriptions of specific embodiments of the present technology have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the present technology and its practical application, to thereby enable others skilled in the art to best utilize the present technology and various embodiments with various modifications as are suited to the particular use contemplated. It is intended that the scope of the invention be defined by the claims appended hereto and their equivalents.

It is appreciated that methods and processes described herein can be performed, in whole or in part, by an engine (e.g., 170, 860, 970, etc.). The methods and processes can be performed in whole or in part in real time, post-facto, on-demand, or some combination thereof, and so on.

What is claimed is:

1. A method comprising:
    accessing respective information associated with monitoring a physical movement of a physical object by one or both of a first actor and a second actor performing an activity, the information including sensed activity information corresponding to a condition/situation associated with movement by the first actor or the second actor, wherein the physical movement of the physical object is associated with manufacture of a product and wherein the sensed activity information is determined in real time by artificial intelligence and includes one or more cycles, one or more processes, one or more tasks, one or more sequences, one or more objects and one or more parameters, in one or more video frame streams;
    creating a multi-dimensional virtual activity space comprising at least three dimensions based on the information, the virtual activity space comprising a virtual representation of the activity;
    comparing the activity performed by one or both of the first actor and the second actor with the virtual representation of the activity in real time by overlaying the activity performed by the one or both of the first actor and the second actor on the virtual representation of the activity;
    analyzing the information in a computer, the analyzing including automated artificial intelligence analysis of the activity associated with the condition/situation, wherein the automated artificial intelligence analysis includes utilizing machine learning back-end unit processes in the analysis to identify a modification of one or more spacings for the first actor and the second actor performing the activity based on reach, motion, action, sequence, and safety zone for the first actor and the second actor; and
    forwarding respective feedback based on results of the analysis to one or both of the first actor and the second actor to avoid the condition/situation, the feedback including adjusting the movement of the first actor or the second actor based on the modification of one or more spacings for the first actor and the second actor performing the activity to avoid interfering with the movement of one another, if the condition/situation is detrimental to the manufacture of the product.

2. The method of claim 1, wherein the feedback includes an individual objective specific to one of either the first actor or the second actor.

3. The method of claim 1, wherein the feedback includes a collective objective with respect to the first actor or the second actor.

4. The method of claim 1, wherein the sensed activity information is associated with a grid within an activity space.

5. The method of claim 1, wherein the first actor is a human and the second actor is a device.

6. The method of claim 1, wherein the first actor is a device and the second actor is a device.

7. The method of claim 1, wherein the first actor is a human and the second actor is a human.

8. The method of claim 1, wherein the feedback is a configuration layout suggestion.

9. The method of claim 1, wherein the feedback is a suggested assignment of a type of actor to the activity.

10. The method of claim 1, further comprising:
    identifying an action that is an ergonomic hazard to one or more human actors based on the sensed activity information from the one or more video frame streams;
    identifying a robot from a library of available robots to perform the ergonomic hazardous action based on the sensed activity information from the one or more video frame streams; and
    forwarding the respective feedback including the identified robot to perform the ergonomic hazardous action in accordance with the modified spacing of the first actor and the second actor for performing the activity.

11. The method of claim 10, further comprising:
    identifying a given action that can be performed more effectively by a given human worker than the one or more robot actors based on the sensed activity information from the one or more video frame streams; and
    forwarding the respective feedback including the identified given human actor to perform the given action in accordance with the modified spacing of the first actor and the second actor for performing the activity.

12. The method of claim 1, further comprising:
    identifying a given action that can be performed more effectively by a given human worker than one or more robot actors based on the sensed activity information from the one or more video frame streams; and
    forwarding the respective feedback including the identified given human actor to perform the given action in accordance with the modified spacing of the first actor and the second actor for performing the activity.

13. A system comprising:
    a data storage unit configured to store information for an engine, including information associated with a station, wherein the station includes a plurality of entities, wherein the plurality of entities includes a first actor and a second actor;
    the engine being configured to:
        access the information regarding monitoring of the station associated with physical movement of an object by one or both of the first actor and the second actor, wherein the information includes sensed activity information corresponding to a condition/situation arising from movement of either the first actor or the second actor and wherein the sensed activity information is determined in real time by artificial intelligence and includes one or more cycles, one or more processes, one or more tasks, one or more sequences, one or more objects and one or more parameters, in one or more video frame streams;
        generate a virtual activity space, the virtual activity space comprising a spatio-temporal representation of a work activity space comprising the station, the virtual activity space comprising kinematics and dynamics associated with the physical movement of the object, the virtual activity space representing at least three dimensions associated with the work activity space;

overlay, in real time, spatial temporal work envelopes of the first actor and the second actor performing activities on the virtual activity space;

perform analytics associated with the one or more of the plurality of entities in the station, including automated artificial intelligence analysis of the respective activities of the first actor and the second actor, wherein the automated artificial intelligence analysis includes utilizing machine learning back-end unit processes in the analysis to identify a modification of one or more spacings for the first actor and the second actor performing the activity based on reach, motion, action, sequence, and safety zone for the first actor and the second actor; and forward feedback to one or both of the first actor and the second actor to avoid the condition/situation, the feedback including adjusting the movement of the first actor or the second actor based on the modification of one or more spacings for the first actor and the second actor performing the activity to avoid interfering with the movement of one another, if the condition/situation is detrimental to the manufacture of the product, wherein the feedback is based on results of the analysis.

14. The system method of claim 13, wherein the analysis includes determination of a work envelope, space utilization, and time/motion determination for both the first actor and the second actor.

15. The system method of claim 13, wherein the analysis includes utilizing representative and probabilistic models for simulation purposes.

16. The system method of claim 13, wherein the analysis includes identification of co-working spaces by overlaying spatial work/task envelope information.

17. The system of claim 13, wherein the activity space is determined based upon reach, motion, and action data.

18. The system of claim 13, wherein the analysis includes utilization of spatio-temporal representations to determine the relative position of an assembly line, the first actor, and the second actor.

19. The system of claim 13, wherein the analysis includes determination of kinematic and dynamic properties of an assembly line, the first actor, and the second actor.

20. The system of claim 13, wherein the analysis includes determination of safer parts of a work envelope.

21. The system method of claim 13, further comprising:
identifying an action that is an ergonomic hazard to one or more human actors based on the sensed activity information from the one or more video frame streams;
identifying a robot from a library of available robots to perform the ergonomic hazardous action based on the sensed activity information from the one or more video frame streams; and
forwarding the respective feedback including the identified robot to perform the ergonomic hazardous action in accordance with the modified spacing of the first actor and the second actor for performing the activity.

22. The system method of claim 21, further comprising:
identifying a given action that can be performed more effectively by a given human worker than the one or more robot actors based on the sensed activity information from the one or more video frame streams; and
forwarding the respective feedback including the identified given human actor to perform the given action in accordance with the modified spacing of the first actor and the second actor for performing the activity.

23. The system method of claim 13, further comprising:
identifying a given action that can be performed more effectively by a given human worker than one or more robot actors based on the sensed activity information from the one or more video frame streams; and
forwarding the respective feedback including the identified given human actor to perform the given action in accordance with the modified spacing of the first actor and the second actor for performing the activity.

24. One or more non-transitory computing device-readable storage media storing instructions executable by one or more computing devices to perform a method comprising:
accessing, in real time, respective information associated with monitoring a first actor and a second actor, the information including sensed activity information corresponding to a condition/situation associated with performance of an activity comprising a movement by either the first actor or the second actor, wherein the sensed activity information is determined in real time by artificial intelligence and includes one or more cycles, one or more processes, one or more tasks, one or more sequences, one or more objects and one or more parameters, in one or more video frame streams;
generating, based on the sensed activity information, a virtual activity space associated with the activity, the virtual activity space comprising grid points associated with grid locations in a real world work space, the virtual activity space comprising three or more dimensions;
overlaying, based on the sensed activity information, the activity performed by the first actor or the second actor on the activity in the virtual activity space as the first actor or the second actor performs the activity;
analyzing the information in real time, including analyzing potential impact of the condition/situation on manufacture of a product to identify a modification of one or more spacings for the first actor and the second actor performing the activity based on reach, motion, action, sequence, and safety zone for the first actor and the second actor; and
forwarding respective feedback in real time based on results of the analysis to one or more of the first actor and the second actor that participate in movement of an object that is associated with manufacture of a product, wherein the feedback is directed to avoidance of the condition/situation, the feedback including adjusting the movement of the first actor or the second actor based on the modification of one or more spacings for the first actor and the second actor performing the activity to avoid interfering with the movement of one another, if the condition/situation is detrimental to the manufacture of the product.

25. The one or more non-transitory computing device-readable storage media method of claim 19, wherein the accessing includes continually sensing activity associated with the first actor and the second actor.

26. The one or more non-transitory computing device-readable storage media of claim 19, wherein the analyzing includes determining activity spaces associated with the first actor and a second actor.

27. The method of claim 24, further comprising:
identifying an action that is an ergonomic hazard to the first actor or the second actor based on the sensed activity information from the one or more video frame streams;

identifying a robot from a library of available robots to perform the ergonomic hazardous action based on the sensed activity information from the one or more video frame streams; and forwarding the respective feedback including the identified robot to perform the ergonomic hazardous action in accordance with the modified spacing of the first actor and the second actor for performing the activity.

28. The method of claim 27, further comprising:

identifying a given action that can be performed more effectively by a given human worker than one or more robot actors based on the sensed activity information from the one or more video frame streams; and forwarding the respective feedback including the identified given human actor to perform the given action in accordance with the modified spacing of the first actor and the second actor for performing the activity.

29. The method of claim 24, further comprising:

identifying a given action that can be performed more effectively by a given human worker than one or more robot actors based on the sensed activity information from the one or more video frame streams; and forwarding the respective feedback including the identified given human actor to perform the given action in accordance with the modified spacing of the first actor and the second actor for performing the activity.

* * * * *